US012544220B2

(12) United States Patent
Essinger et al.

(10) Patent No.: US 12,544,220 B2
(45) **Date of Patent: *Feb. 10, 2026**

(54) AORTIC BIOPROSTHESIS AND SYSTEMS FOR DELIVERY THEREOF

(71) Applicant: Symetis SA, Ecublens (CH)

(72) Inventors: Jacques Essinger, Wollerau (CH); Youssef Biadillah, Munich (DE); Stephane Delaloye, Bulach (CH); Jean-Luc Hefti, Cheseaux-Noreaz (CH); Luc Mantanus, Lausanne (CH); Reynald Passerini, Lausanne (CH)

(73) Assignee: Symetis SA, Ecublens (CH)

( * ) Notice: Subject to any disclaimer, the term of this patent is extended or adjusted under 35 U.S.C. 154(b) by 357 days.

This patent is subject to a terminal disclaimer.

(21) Appl. No.: 18/079,240

(22) Filed: Dec. 12, 2022

(65) Prior Publication Data

US 2023/0113881 A1 Apr. 13, 2023

Related U.S. Application Data

(63) Continuation of application No. 16/511,527, filed on Jul. 15, 2019, now abandoned, which is a continuation of application No. 13/505,195, filed as application No. PCT/EP2010/063306 on Sep. 10, 2010, now Pat. No. 10,376,359.

(60) Provisional application No. 61/353,875, filed on Jun. 11, 2010, provisional application No. 61/257,230, filed on Nov. 2, 2009.

(51) Int. Cl.
*A61F 2/24* (2006.01)

(52) U.S. Cl.
CPC .......... *A61F 2/2412* (2013.01); *A61F 2/2418* (2013.01); *A61F 2/2436* (2013.01); *A61F 2220/0058* (2013.01); *A61F 2230/0054* (2013.01)

(58) Field of Classification Search
CPC .... A61F 2/2412; A61F 2/2418; A61F 2/2436; A61F 2220/0058; A61F 2230/0054
See application file for complete search history.

(56) References Cited

U.S. PATENT DOCUMENTS

| | | | |
|---|---|---|---|
| 3,755,823 | A | 9/1973 | Hancock |
| 4,106,129 | A | 8/1978 | Carpentier et al. |
| 4,470,157 | A | 9/1984 | Love |

(Continued)

FOREIGN PATENT DOCUMENTS

| | | | |
|---|---|---|---|
| AU | 2006328896 | A1 | 6/2007 |
| AU | 2007294199 | A1 | 3/2008 |
| AU | 2009200985 | A1 | 4/2009 |

(Continued)

OTHER PUBLICATIONS

The International Search Report and Written Opinion of the International Searching Authority for International Application No. PCT/EP2010/063306.

(Continued)

*Primary Examiner* — Ashley L Fishback
*Assistant Examiner* — Chima U Igboko
(74) *Attorney, Agent, or Firm* — Seager, Tufte & Wickhem LLP

(57) ABSTRACT

Embodiments of the present disclosure are directed to stents, valved-stents, and associated methods and systems for their delivery via minimally-invasive surgery.

19 Claims, 16 Drawing Sheets

(56) References Cited

U.S. PATENT DOCUMENTS

| | | | |
|---|---|---|---|
| 5,078,720 | A | 1/1992 | Burton et al. |
| 5,163,955 | A | 11/1992 | Love et al. |
| 5,192,301 | A | 3/1993 | Kamiya et al. |
| 5,344,442 | A | 9/1994 | Deac |
| 5,354,330 | A | 10/1994 | Hanson et al. |
| 5,411,552 | A | 5/1995 | Andersen et al. |
| 5,480,424 | A | 1/1996 | Cox |
| 5,499,995 | A | 3/1996 | Teirstein |
| 5,500,015 | A | 3/1996 | Deac |
| 5,540,712 | A | 7/1996 | Kleshinski et al. |
| 5,571,174 | A | 11/1996 | Love et al. |
| 5,609,626 | A | 3/1997 | Quijano et al. |
| 5,653,749 | A | 8/1997 | Love et al. |
| 5,662,703 | A | 9/1997 | Yurek et al. |
| 5,713,950 | A | 2/1998 | Cox |
| 5,718,725 | A | 2/1998 | Sterman et al. |
| 5,769,882 | A | 6/1998 | Fogarty et al. |
| 5,797,960 | A | 8/1998 | Stevens et al. |
| 5,807,327 | A | 9/1998 | Green et al. |
| 5,817,126 | A | 10/1998 | Imran |
| 5,823,956 | A | 10/1998 | Roth et al. |
| 5,824,041 | A | 10/1998 | Enker et al. |
| 5,840,081 | A | 11/1998 | Andersen et al. |
| 5,855,600 | A | 1/1999 | Alt |
| 5,855,601 | A | 1/1999 | Bessler et al. |
| 5,861,028 | A | 1/1999 | Angell |
| 5,938,697 | A | 8/1999 | Killion et al. |
| 5,957,949 | A | 9/1999 | Leonhardt et al. |
| 5,976,174 | A | 11/1999 | Ruiz |
| 5,980,533 | A | 11/1999 | Holman |
| 6,029,671 | A | 2/2000 | Stevens et al. |
| 6,083,257 | A | 7/2000 | Taylor et al. |
| 6,102,944 | A | 8/2000 | Huynh et al. |
| 6,110,201 | A | 8/2000 | Quijano et al. |
| 6,168,614 | B1 | 1/2001 | Andersen et al. |
| 6,171,335 | B1 | 1/2001 | Wheatley et al. |
| 6,183,481 | B1 | 2/2001 | Lee et al. |
| 6,196,230 | B1 | 3/2001 | Hall et al. |
| 6,214,036 | B1 | 4/2001 | Letendre et al. |
| 6,231,602 | B1 | 5/2001 | Carpentier et al. |
| 6,254,564 | B1 | 7/2001 | Wilk et al. |
| 6,287,334 | B1 | 9/2001 | Moll et al. |
| 6,287,339 | B1 | 9/2001 | Vazquez et al. |
| 6,331,189 | B1 | 12/2001 | Wolinsky et al. |
| 6,350,278 | B1 | 2/2002 | Enker et al. |
| 6,379,383 | B1 | 4/2002 | Palmaz et al. |
| 6,406,493 | B1 | 6/2002 | Tu et al. |
| 6,409,759 | B1 | 6/2002 | Peredo |
| 6,454,799 | B1 | 9/2002 | Schreck |
| 6,458,153 | B1 | 10/2002 | Bailey et al. |
| 6,530,952 | B2 | 3/2003 | Vesely |
| 6,533,807 | B2 | 3/2003 | Wolinsky et al. |
| 6,537,310 | B1 | 3/2003 | Palmaz et al. |
| 6,562,069 | B2 | 5/2003 | Cai et al. |
| 6,569,196 | B1 | 5/2003 | Vesely |
| 6,572,652 | B2 | 6/2003 | Shaknovich |
| 6,582,462 | B1 | 6/2003 | Andersen et al. |
| 6,589,279 | B1 | 7/2003 | Anderson et al. |
| 6,613,079 | B1 | 9/2003 | Wolinsky et al. |
| 6,635,085 | B1 | 10/2003 | Caffey et al. |
| 6,652,555 | B1 | 11/2003 | VanTassel et al. |
| 6,682,558 | B2 | 1/2004 | Tu et al. |
| 6,682,559 | B2 | 1/2004 | Myers et al. |
| 6,695,865 | B2 | 2/2004 | Boyle et al. |
| 6,719,787 | B2 | 4/2004 | Cox |
| 6,730,118 | B2 | 5/2004 | Spenser et al. |
| 6,733,525 | B2 | 5/2004 | Yang et al. |
| 6,736,827 | B1 | 5/2004 | McAndrew et al. |
| 6,755,855 | B2 | 6/2004 | Yurek et al. |
| 6,767,362 | B2 | 7/2004 | Schreck |
| 6,790,229 | B1 | 9/2004 | Berreklouw |
| 6,805,711 | B2 | 10/2004 | Quijano et al. |
| 6,830,584 | B1 | 12/2004 | Seguin |
| 6,830,585 | B1 | 12/2004 | Artof et al. |
| 6,830,586 | B2 | 12/2004 | Quijano et al. |
| 6,849,085 | B2 | 2/2005 | Marton |
| 6,875,231 | B2 | 4/2005 | Anduiza et al. |
| 6,893,460 | B2 | 5/2005 | Spenser et al. |
| 6,908,481 | B2 | 6/2005 | Cribier |
| 6,936,066 | B2 | 8/2005 | Palmaz et al. |
| 6,942,682 | B2 | 9/2005 | Vrba et al. |
| 7,018,406 | B2 | 3/2006 | Seguin et al. |
| 7,025,773 | B2 | 4/2006 | Gittings et al. |
| 7,025,780 | B2 | 4/2006 | Gabbay |
| 7,041,132 | B2 | 5/2006 | Quijano et al. |
| 7,044,966 | B2 | 5/2006 | Svanidze et al. |
| 7,101,396 | B2 | 9/2006 | Artof et al. |
| 7,141,064 | B2 | 11/2006 | Scott et al. |
| 7,179,290 | B2 | 2/2007 | Cao |
| 7,195,641 | B2 | 3/2007 | Palmaz et al. |
| 7,198,646 | B2 | 4/2007 | Figulla et al. |
| 7,201,772 | B2 | 4/2007 | Schwammenthal et al. |
| 7,217,287 | B2 | 5/2007 | Wilson et al. |
| 7,252,682 | B2 | 8/2007 | Seguin |
| 7,276,078 | B2 | 10/2007 | Spenser et al. |
| 7,285,130 | B2 | 10/2007 | Austin |
| 7,316,712 | B2 | 1/2008 | Peredo |
| 7,318,278 | B2 | 1/2008 | Zhang et al. |
| 7,320,704 | B2 | 1/2008 | Lashinski et al. |
| 7,320,705 | B2 | 1/2008 | Quintessenza |
| 7,329,278 | B2 | 2/2008 | Seguin et al. |
| 7,329,279 | B2 | 2/2008 | Haug et al. |
| 7,331,991 | B2 | 2/2008 | Kheradvar et al. |
| 7,331,993 | B2 | 2/2008 | White |
| 7,338,484 | B2 | 3/2008 | Schoon et al. |
| 7,361,189 | B2 | 4/2008 | Case et al. |
| 7,371,258 | B2 | 5/2008 | Woo et al. |
| 7,374,571 | B2 | 5/2008 | Pease et al. |
| 7,377,938 | B2 | 5/2008 | Sarac et al. |
| 7,381,218 | B2 | 6/2008 | Schreck |
| 7,381,219 | B2 | 6/2008 | Salahieh et al. |
| 7,393,358 | B2 | 7/2008 | Malewicz |
| 7,393,360 | B2 | 7/2008 | Spenser et al. |
| 7,399,315 | B2 | 7/2008 | Iobbi |
| 7,402,171 | B2 | 7/2008 | Osborne et al. |
| 7,410,499 | B2 | 8/2008 | Bicer |
| 7,416,530 | B2 | 8/2008 | Turner et al. |
| 7,422,603 | B2 | 9/2008 | Lane |
| 7,431,733 | B2 | 10/2008 | Knight |
| 7,435,257 | B2 | 10/2008 | Ashinski et al. |
| 7,445,632 | B2 | 11/2008 | McGuckin, Jr. et al. |
| 7,455,689 | B2 | 11/2008 | Johnson |
| 7,470,284 | B2 | 12/2008 | Lambrecht et al. |
| 7,470,285 | B2 | 12/2008 | Nugent et al. |
| 7,473,275 | B2 | 1/2009 | Marquez |
| 7,481,838 | B2 | 1/2009 | Carpentier et al. |
| 7,500,989 | B2 | 3/2009 | Solem et al. |
| 7,503,929 | B2 | 3/2009 | Johnson et al. |
| 7,503,930 | B2 | 3/2009 | Sharkawy et al. |
| 7,510,572 | B2 | 3/2009 | Gabbay |
| 7,510,575 | B2 | 3/2009 | Spenser et al. |
| 7,513,909 | B2 | 4/2009 | Lane et al. |
| 7,534,261 | B2 | 5/2009 | Friedman |
| 7,556,646 | B2 | 7/2009 | Yang et al. |
| 7,578,828 | B2 | 8/2009 | Gittings et al. |
| 7,585,321 | B2 | 9/2009 | Cribier |
| 7,591,848 | B2 | 9/2009 | Allen |
| 7,618,446 | B2 | 11/2009 | Andersen et al. |
| 7,625,403 | B2 | 12/2009 | Krivoruchko |
| 7,632,296 | B2 | 12/2009 | Malewicz |
| 7,682,390 | B2 | 3/2010 | Seguin |
| 7,780,726 | B2 | 8/2010 | Seguin |
| 7,846,203 | B2 | 12/2010 | Cribier |
| 7,846,204 | B2 | 12/2010 | Letac et al. |
| 7,896,915 | B2 | 3/2011 | Guyenot et al. |
| 7,914,575 | B2 | 3/2011 | Guyenot et al. |
| 7,947,075 | B2 | 5/2011 | Goetz et al. |
| 7,959,672 | B2 | 6/2011 | Salahieh et al. |
| 8,002,825 | B2 | 8/2011 | Letac et al. |
| 8,052,749 | B2 | 11/2011 | Salahieh et al. |
| 8,057,540 | B2 | 11/2011 | Letac et al. |
| 8,092,518 | B2 | 1/2012 | Schreck |
| 8,092,520 | B2 | 1/2012 | Quadri |
| 8,603,159 | B2 | 12/2013 | Seguin et al. |

(56) References Cited

U.S. PATENT DOCUMENTS

| | | | |
|---|---|---|---|
| 8,628,571 | B1 | 1/2014 | Hacohen et al. |
| 8,647,381 | B2 | 2/2014 | Essinger et al. |
| 8,845,721 | B2 | 9/2014 | Braido et al. |
| 10,376,359 | B2 | 8/2019 | Essinger et al. |
| 2002/0032481 | A1 | 3/2002 | Gabbay |
| 2002/0177894 | A1 | 11/2002 | Acosta et al. |
| 2003/0028213 | A1 | 2/2003 | Thill et al. |
| 2003/0040792 | A1 | 2/2003 | Gabbay |
| 2003/0042186 | A1 | 3/2003 | Boyle |
| 2004/0019374 | A1 | 1/2004 | Hojeibane et al. |
| 2004/0044361 | A1 | 3/2004 | Frazier et al. |
| 2004/0044400 | A1 | 3/2004 | Cheng et al. |
| 2004/0092858 | A1 | 5/2004 | Wilson et al. |
| 2004/0093063 | A1 | 5/2004 | Wright et al. |
| 2004/0210304 | A1 | 10/2004 | Seguin et al. |
| 2004/0254594 | A1 | 12/2004 | Alfaro |
| 2004/0260389 | A1 | 12/2004 | Case et al. |
| 2005/0043759 | A1 | 2/2005 | Chanduszko |
| 2005/0070794 | A1 | 3/2005 | Deal et al. |
| 2005/0113910 | A1 | 5/2005 | Paniagua et al. |
| 2005/0137681 | A1 | 6/2005 | Shoemaker et al. |
| 2005/0137688 | A1 | 6/2005 | Salahieh et al. |
| 2005/0137695 | A1 | 6/2005 | Salahieh et al. |
| 2005/0137696 | A1 | 6/2005 | Salahieh et al. |
| 2005/0137701 | A1 | 6/2005 | Salahieh et al. |
| 2005/0137702 | A1 | 6/2005 | Haug et al. |
| 2005/0182483 | A1 | 8/2005 | Osborne et al. |
| 2005/0267523 | A1 | 12/2005 | Devellian et al. |
| 2005/0283231 | A1 | 12/2005 | Haug et al. |
| 2005/0288706 | A1 | 12/2005 | Widomski et al. |
| 2006/0004442 | A1 | 1/2006 | Spenser et al. |
| 2006/0122692 | A1 | 6/2006 | Gilad et al. |
| 2006/0149360 | A1 | 7/2006 | Schwammenthal et al. |
| 2006/0161248 | A1 | 7/2006 | Case et al. |
| 2006/0259136 | A1 | 11/2006 | Nguyen et al. |
| 2006/0259137 | A1 | 11/2006 | Artof et al. |
| 2006/0287717 | A1 | 12/2006 | Rowe et al. |
| 2007/0060998 | A1 | 3/2007 | Butterwick et al. |
| 2007/0061002 | A1 | 3/2007 | Paul et al. |
| 2007/0198097 | A1 | 8/2007 | Zegdi |
| 2007/0213813 | A1 | 9/2007 | Von Segesser et al. |
| 2007/0239265 | A1 | 10/2007 | Birdsall |
| 2007/0239269 | A1 | 10/2007 | Dolan et al. |
| 2007/0244546 | A1 | 10/2007 | Francis |
| 2007/0282436 | A1 | 12/2007 | Pinchuk |
| 2008/0033541 | A1 | 2/2008 | Gelbart et al. |
| 2008/0071361 | A1 | 3/2008 | Tuval et al. |
| 2008/0071362 | A1 | 3/2008 | Tuval et al. |
| 2008/0071366 | A1 | 3/2008 | Tuval et al. |
| 2008/0071368 | A1 | 3/2008 | Tuval et al. |
| 2008/0077234 | A1 | 3/2008 | Styrc |
| 2008/0125859 | A1 | 5/2008 | Salahieh et al. |
| 2008/0140189 | A1 | 6/2008 | Nguyen et al. |
| 2008/0161909 | A1 | 7/2008 | Kheradvar et al. |
| 2008/0177381 | A1 | 7/2008 | Navia et al. |
| 2008/0195199 | A1 | 8/2008 | Kheradvar et al. |
| 2008/0208327 | A1 | 8/2008 | Rowe |
| 2008/0228263 | A1 | 9/2008 | Ryan |
| 2008/0234814 | A1 | 9/2008 | Salahieh et al. |
| 2008/0255660 | A1 | 10/2008 | Guyenot et al. |
| 2008/0269878 | A1 | 10/2008 | Iobbi |
| 2008/0275550 | A1 | 11/2008 | Kheradvar et al. |
| 2009/0005863 | A1 | 1/2009 | Goetz et al. |
| 2009/0054976 | A1 | 2/2009 | Tuval et al. |
| 2009/0164006 | A1 | 6/2009 | Seguin et al. |
| 2009/0171432 | A1 | 7/2009 | Von Segesser et al. |
| 2009/0171447 | A1 | 7/2009 | Von Segesser et al. |
| 2009/0276040 | A1 | 11/2009 | Rowe et al. |
| 2009/0287299 | A1 * | 11/2009 | Tabor .................... A61F 2/2418 623/1.26 |
| 2010/0168839 | A1 | 7/2010 | Braido et al. |
| 2010/0185277 | A1 | 7/2010 | Braido et al. |
| 2010/0256723 | A1 | 10/2010 | Murray |
| 2011/0022157 | A1 * | 1/2011 | Essinger ............... A61F 2/2436 623/1.11 |
| 2011/0029072 | A1 | 2/2011 | Gabbay |
| 2011/0040374 | A1 | 2/2011 | Goetz et al. |
| 2011/0224780 | A1 | 9/2011 | Tabor et al. |
| 2012/0101571 | A1 | 4/2012 | Thambar et al. |
| 2012/0101572 | A1 | 4/2012 | Kovalsky et al. |
| 2012/0116496 | A1 | 5/2012 | Chuter et al. |
| 2012/0123529 | A1 | 5/2012 | Levi et al. |
| 2012/0172982 | A1 | 7/2012 | Stacchino et al. |
| 2012/0303116 | A1 | 11/2012 | Gorman, III et al. |

FOREIGN PATENT DOCUMENTS

| | | | |
|---|---|---|---|
| CA | 2634358 | A1 | 6/2007 |
| CA | 2657839 | A1 | 3/2008 |
| CA | 2659690 | A1 | 3/2008 |
| DE | 20003874 | U1 | 5/2000 |
| DE | 19857887 | A1 | 7/2000 |
| DE | 102005003632 | A1 | 8/2006 |
| DE | 202007005491 | U1 | 6/2007 |
| EP | 0592410 | A1 | 11/1991 |
| EP | 0657147 | A2 | 6/1995 |
| EP | 0696447 | A2 | 2/1996 |
| EP | 0943302 | A2 | 9/1999 |
| EP | 1093771 | A2 | 4/2001 |
| EP | 1251797 | A1 | 10/2002 |
| EP | 1262201 | A1 | 12/2002 |
| EP | 1264582 | A2 | 12/2002 |
| EP | 1267753 | A2 | 1/2003 |
| EP | 1598031 | A2 | 11/2005 |
| EP | 1968491 | A2 | 9/2008 |
| EP | 2033593 | A1 | 3/2009 |
| EP | 2047824 | A1 | 4/2009 |
| EP | 2059192 | A1 | 5/2009 |
| EP | 2074964 | A1 | 7/2009 |
| FR | 2874812 | A1 | 3/2006 |
| WO | 9829057 | A1 | 7/1998 |
| WO | 0028922 | A1 | 5/2000 |
| WO | 0047139 | A1 | 8/2000 |
| WO | 0053122 | A1 | 9/2000 |
| WO | 0149213 | A2 | 7/2001 |
| WO | 0162189 | A1 | 8/2001 |
| WO | 02067782 | A2 | 9/2002 |
| WO | 02076349 | A1 | 10/2002 |
| WO | 03003949 | A2 | 1/2003 |
| WO | 03047468 | A1 | 6/2003 |
| WO | 03063729 | A2 | 8/2003 |
| WO | 03003949 | A3 | 1/2004 |
| WO | 2005010215 | A2 | 2/2005 |
| WO | 2005070343 | A1 | 8/2005 |
| WO | 2006058163 | A2 | 6/2006 |
| WO | 2006068944 | A2 | 6/2006 |
| WO | 2006076890 | A1 | 7/2006 |
| WO | 2006083763 | A1 | 8/2006 |
| WO | 2006086135 | A2 | 8/2006 |
| WO | 2006086736 | A2 | 8/2006 |
| WO | 2006127765 | A1 | 11/2006 |
| WO | 2007071436 | A2 | 6/2007 |
| WO | 2007071436 | A3 | 11/2007 |
| WO | 2008028569 | A1 | 3/2008 |
| WO | 2008040555 | A2 | 4/2008 |
| WO | 2008070442 | A1 | 6/2008 |
| WO | 2009024859 | A2 | 2/2009 |
| WO | 2009053497 | A1 | 4/2009 |
| WO | 2009091509 | A1 | 7/2009 |
| WO | 2010045238 | A2 | 4/2010 |
| WO | 2010045297 | A2 | 4/2010 |
| WO | 2010049160 | A1 | 5/2010 |
| WO | 2010083558 | A1 | 7/2010 |
| WO | 2011051043 | A1 | 5/2011 |
| WO | 2011057087 | A1 | 5/2011 |
| WO | 2013033791 | A1 | 3/2013 |
| WO | 2013134214 | A1 | 9/2013 |
| WO | 2014072439 | A1 | 5/2014 |

OTHER PUBLICATIONS

Weerasinghe et al., "First Redo Heart Valve Replacement: A 10-Year Analysis", Circulation (1999), 99:655-658.

(56) References Cited

OTHER PUBLICATIONS

Examination Report dated Feb. 6, 2009 for European Application No. 06841127.1 filed Dec. 22, 2006.
European Search Report dated May 29, 2009 for European Application No. 09154935.2, filed Aug. 23, 2007.
Australian Examination Report dated Mar. 4, 2010 for Australian Application No. 2009200985.
European Examination Report dated Aug. 11, 2009 for European Application No. 07818037.9, filed Aug. 23, 2007.
International Preliminary Report on Patentability dated Mar. 10, 2009 for PCT/EP/2007/007413, filed Aug. 23, 2007.
International Search Report dated Mar. 25, 2009 and Written Opinion for Application No. PCT/EP2008/064558, filed Oct. 27, 2008.
International Search Report dated Sep. 27, 2007 for PCT/EP2006/012455, filed Dec. 22, 2006.
Partial International Search Report dated Mar. 13, 2014 for PCT/EP2014/055044 filed Mar. 13, 2014.
International Search Report dated Apr. 15, 2009 and Written Opinion for Application No. PCT/IB2008/002180, filed Aug. 21, 2008.
International Preliminary Report on Patentability dated Feb. 24, 2010 for PCT/IB2008/002180, filed Aug. 21, 2008.
International Search Report dated Sep. 12, 2010 for Application No. PCT/EP2010/057798, filed Jun. 3, 2010.
International Preliminary Report on Patentability dated Dec. 6, 2011 for Application No. PCT/EP2010/057798, filed Jun. 3, 2010.
International Search Report dated Jan. 28, 2008 for Application No. PCT/EP2007/007413, filed Aug. 23, 2007.
International Preliminary Report on Patentability dated Jun. 24, 2008 for PCT/EP2006/012455, filed Dec. 22, 2006.
International Preliminary Report on Patentability dated May 8, 2012 for Application No. PCT/EP2010/063306, filed Sep. 10, 2010.
International Search Report dated Feb. 17, 2012 for Application No. PCT/EP2011/066677, filed Sep. 26, 2011.
International Preliminary Report on Patentability dated Mar. 26, 2013 for PCT/EP2011/066677, filed Sep. 26, 2011.
International Search Report dated Apr. 17, 2014 for PCT/EP2013/073318, filed Nov. 8, 2013.
Atkins et al., "Risk of Preoperative Valve Replacement for Failed Mitral and Aortic Bioprostheses", Ann Thorac Surg (1998), 65: 1545-52.
Ma et al., "Double-crowned valved stents for off-pump mitral valve replacement", European Journal of Cardio-Thoracic Surgery (2005), 28:194-199.
Walther et al., "Transapical approach for sutureless stent-fixed aortic valve implantation: experimental results", European Journal of Cardiao-thoracic Surgery 29 (2006), 703-708.
Mack, "Minimally invasive cardiac surgery", Surg Endosc, (2006) 20:S488-S492.
Dewey et al., "Transapical aortic valve implantation: an animal feasibility study", The annals of thoracic surgery, (2006): 82:110-116.
Pawelec-Wojtalk "Closure of left ventricle perforation with the use of muscular VSD occulder", European Journal of Cardio-Thoracic Surgery (2005), 27:714-716.
Definition: Apex; https://www.merriam-webster.com/dictionary/apex; Aug. 1, 2018; apex_definition.pdf.

* cited by examiner

AORTIC BIOPROSTHESIS AND SYSTEMS FOR DELIVERY THEREOF

CROSS-REFERENCE TO RELATED APPLICATIONS

This application is a continuation of U.S. application Ser. No. 16/511,527, filed Jul. 15, 2019, which is a continuation of U.S. application Ser. No. 13/505,195, filed Jul. 11, 2012; which is a 371 National Stage of International Application No. PCT/EP2010/063306, filed Sep. 10, 2010; which claims the benefit of priority of U.S. Provisional Patent Application No. 61/257,230, filed Nov. 2, 2009, and U.S. Provisional Patent Application No. 61/353,875, filed Jun. 11, 2010 the entire disclosures of which are incorporated herein by reference in their entireties.

FIELD OF THE DISCLOSURE

Embodiments of the present disclosure are directed to systems, methods, and devices for cardiac valve replacement in mammalian hearts.

BACKGROUND OF THE DISCLOSURE

Conventional approaches for cardiac valve replacement require the cutting of a relatively large opening in the patient's sternum ("sternotomy") or thoracic cavity ("thoracotomy") in order to allow the surgeon to access the patient's heart. Additionally, these approaches require arrest of the patient's heart and a cardiopulmonary bypass (i.e., use of a heart-lung bypass machine to oxygenate and circulate the patient's blood). In recent years, efforts have been made to establish a less invasive cardiac valve replacement procedure, by delivering and implanting a cardiac replacement valve via a catheter percutaneously (i.e., through the skin) via either a transvascular approach delivering the new valve through the femoral artery, or by transapical route, where the replacement valve is delivered between ribs and directly through the wall of the heart to the implantation site.

While less invasive and arguably less complicated, percutaneous heart valve replacement therapies (PHVT) still have various shortcomings, including the inability for a surgeon to ensure proper positioning and stability of the replacement valve within the patient's body. Specifically, if the replacement valve is not placed in the proper position relative to the implantation site, it can lead to poor functioning of the valve. For example, in an aortic valve replacement, if the replacement valve is placed too high, it can lead to valve regurgitation, instability, valve prolapse and/or coronary occlusion. If the valve is placed too low, it can also lead to regurgitation and mitral valve interaction.

To address such risks, recapture procedures and systems have been developed. For example, such a system is disclosed in U.S. publication no. 20050137688 and U.S. Pat. No. 5,957,949, each disclosure of which is herein incorporated by reference. While such systems may address the problem of improper placement, they are somewhat complicated, requiring the use of wires which are removable attached to an end of the stent to pull the stent back into the delivery catheter.

Throughout this description, including the foregoing description of related art, any and all publicly available documents described herein, including any and all U. S. patents, are specifically incorporated by reference herein in their entirety. The foregoing description of related art is not intended in any way as an admission that any of the documents described therein, including pending United States patent applications, are prior art to embodiments according to the present disclosure. Moreover, the description herein of any disadvantages associated with the described products, methods, and/or apparatus, is not intended to limit inventions disclosed herein. Indeed, aspects of the disclosed embodiments may include certain features of the described products, methods, and/or apparatus without suffering from their described disadvantages.

SUMMARY OF THE DISCLOSURE

In some embodiments, a replacement valve for use within a human body is provided, where the replacement valve includes a valve component and a stent component (the replacement valve also being referred to as a valved-stent or a stent(-) valve, and may be used interchangeably with replacement valve throughout the disclosure). The stent component defines a first (e.g., proximal) end and a second (e.g., distal) end and may include a plurality of stent sections.

The proximal end P of the stent component may be described as the end of the stent component/replacement valve which ultimately is positioned adjacent and/or within the left ventricle. The proximal end P of the stent component may comprise one or more anchoring or attachment elements for attachment to the delivery catheter (e.g., attachment end in a transapical delivery system). The distal end D of the stent component may be described as the end of the replacement valve/stent component which ultimately is positioned adjacent and/or near the ascending aorta, when, for example, the delivery catheter is advanced toward/into the ascending aorta in a transapical delivery system. The distal end sometimes is referred to as the aortic end and the proximal end is sometimes referred to as the ventricular end. According to preferred embodiments of the disclosure, the replacement valves according to at least some embodiments are released distal-to-proximal, that is, the end of the stent (replacement valve) which ultimately is positioned within/near/adjacent the aorta is released before the end of the stent (replacement valve) which ultimately is positioned within/near/adjacent the ventricle is released last. Such a delivery, according to preferred embodiments, is via a transapical approach, or through the heart muscle (as opposed to being delivered transvascularly). While preferred embodiments disclosed herein are described as being delivered through a direct heart access approach (e.g., transapical approach using transapical/direct access delivery systems), some embodiments of the present invention may be delivered transvascularly (e.g.,transfemorally).

According to some embodiments, there is provided a replacement valve for use within a human body comprising: a valve component; and a stent component configured to house at least a portion of the valve component comprising a proximal end and a distal end, the stent component further comprising a lower anchoring crown comprising an at least partly conical body, where the lower anchoring crown defines the proximal end of the stent component; an upper anchoring crown in communication with the lower anchoring crown and comprising an at least partly conical body, where the conical body of the lower anchoring crown slopes outwardly in the direction of the proximal end, and the conical body of the upper anchoring crown slopes outwardly in the direction of the distal end; the distal stent section comprising an at least partly conical body, where the distal stent section is in communication with the upper anchoring crown, preferably the distal stent section comprises a conical or cylindrical commissural post section and a stabilization arch section, where the commissural post section is in communication with the upper anchoring crown; and the stabilization arch section is in communication with a commissural post section and comprises an at least partly conical body, and where the stabilization arch section defines the distal end. In some embodiments, at least a partially cylindrical body of commissural post section comprises valve fixation elements. The stent component may be formed from a single tube or sheet of metal.

In this context the term "partly conical body" shall mean that the crown may have any divergent shape. The upper and/or the lower anchoring crown may include a plurality of subsequent conical sections with different inclinations or may have a continuously increasing or decreasing divergence, e.g. may have a trumpet-mouth like shape. The upper and/or the lower anchoring crown may also include one or more cylindrical sections or inwardly converging sections.

The upper and lower anchoring crown may meet at a line where the stent has a minimal diameter.

In some embodiments the commissural post section meets the lower and/or upper anchoring crown at the same line, where the upper anchoring crown meets the lower anchoring crown.

The conical body of the lower anchoring crown may slope outwardly from an inner diameter D2 to an outer diameter D3 in the direction of the proximal end, where the inner diameter D2 is between about 20 mm to about 30 mm, and the outer diameter D3 is between about 22 mm to about 40 mm. The axial distance between the planes of the diameters D2 and D3 in the expanded configuration may be between about 3 to about 15 mm. The outward slope of the lower anchoring crown may be defined by an angle $\alpha$2, where $\alpha$2 is between from about 5 degree to about 50 degree.

The conical body of the upper anchoring crown slopes outwardly from an inner diameter D2 to an outer diameter D1 in the direction of the distal end, where the inner diameter D2 may be between about 20 mm to about 30 mm, and the outer diameter D1 is between about 22 mm to about 40 mm.

The axial distance between the planes of the diameters D2 and D1 in the expanded configuration may be between about 3 to about 10 mm.

The outward slope of the upper anchoring crown may be defined by an angle $\alpha$1, where $\alpha$1 is between from about 10 degree to about 80 degree.

In some embodiments, the end of the upper anchoring crown forms a tip, where the tip is bent inwardly toward the longitudinal axis at an angle $\alpha$3 as compared to the direction of the crown surface, and a3 is between from about 0 degree to about 180 degree. The length of the combined upper anchoring crown and commissural post section of the stent component H3 may be between about 3 to about 50 mm. The length of the stabilization arches and of the stent component H4 may be between about 5 to about 50 mm.

In some embodiments the upper and/or lower crown may include a cylindrical or only slightly outwardly sloping section, thus there is a substantially cylindrical section between the actually diverging part of the upper conical crown and the actually diverging part of the lower conical crown. The substantially cylindrical section sometimes is referred to as the trunk section The axial length of the trunk section may be greater than 3 mm. Additionally or alternatively, the length of the trunk section may be less than 7 mm. For example, the axial length of the trunk section may be between 4 and 6 mm.

In some embodiments the axial length of the substantially cylindrical section is at least 50% of the axial length of at least one of the lower or upper anchoring crown and/or wherein the axial length of the substantially cylindrical section is equal to or greater than the axial length of at least one of the first and second sections.

In context with the present application substantially cylindrical or only slightly outwardly sloping sections are sections having an inclination angle of less than 10 degree with respect to the axis of the stent.

In some embodiments, the lower anchoring crown is configured to create a form fit with an inflow of an aortic valve and thus prevent migration of the stent component and the valve component towards the ascending aorta.

In some embodiments, the upper anchoring crown is configured to create a form fit with an outflow tract and native leaflets of an aortic valve and thus prevent migration of the stent component and the valve component towards the left ventricle.

In some embodiments the tips of the upper anchoring crown may rest in a final position on or against the pushed back native valve leaflets and thus prevent migration of the stent component and the valve component towards the ascending aorta and/or towards the left ventricle.

In some embodiments, the commissural post section comprises a plurality of commissural posts configured for fixation to commissures of the valve component.

In one embodiment the distal stent section comprises a plurality of stabilization arches for bearing against the ascending aorta for alignment of the stent-component with respect to the ascending aorta, each stabilization arch comprises a divergent portion that diverges away from the stent axis, in a direction towards the distal end; and an arch apex inclined at an angle (a5) measured from the divergent portion in a direction towards the stent axis.

In some embodiments, the stabilization arches or loops are configured to engage the ascending aorta to orient the stent component, the valve component, and an associated delivery system longitudinally within an aorta/aortic annulus thus preventing tilting of the stent component and the valve component during the implantation procedure and/or when implanted.

In some embodiments at least one limb (or strut) of at least one arch comprises an asymmetric feature. Preferably the limb comprises a pattern, for example one or more kinks, such that the limb is different from another limb of the arch and may be distinguished from the other limb in a projected image. The asymmetric feature may provide information about the rotational alignment during implantation for example when observed on an X-ray projection.

Alternatively or additionally there may be at least one asymmetric feature in a cell of the upper or lower crown.

In some embodiments, the lower anchoring crown comprises at least one attachment element for removable attachment to a delivery device.

In some embodiments the (or at least one) attachment element is formed generally in the form of an opening which is able to enlarge when the stent component radially expands. The opening is adapted to receive a pin arranged on the stent holder.

In particular the attachment element may be formed by an axial elongation of at least one cell of the lower crown. Preferably three attachment elements are formed by three such elongated cells, optionally equally spaced around the perimeter. Preferably the or each elongated element is adapted to receive a respective pin projecting radially on the stent holder.

In some embodiments the attachment element may be formed generally in the shape of a hook. In particular the attachment element is formed by an elongation of at least one cell of the lower crown which is inwardly inclined and/or bent. Preferably three attachment elements are formed by three such elongated cells, optionally equally spaced around the perimeter of the stent and bent inwardly. The or each inclined attachment element may be adapted to be received by a groove arranged on a stent holder and/or to engage a respective pin extending or projecting axially on the stent holder.

In some embodiments, the stent component comprises a plurality of commissural posts for fixation to a corresponding plurality of valve commissures.

In some embodiments of the present disclosure, a stent component may be provided that includes a central, longitudinal axis and at least one attachment element for removable attachment to a delivery device. The at least one attachment element may be formed generally in the shape of a hook extending inwardly towards the central, longitudinal axis. The delivery device may include a stent holder comprising a groove for receiving the attachment element of the stent component, where release of the stent-valve from the stent holder may be facilitated by rotation of the stent holder relative to the attachment element.

In still other embodiments of the present disclosure, a replacement valve for use within a human body is provided that includes a valve component, a stent component for housing the valve component, and at least two skirts (e.g., polyester (PET) skirts). An inner skirt may be provided that covers at least a portion (e.g., all) of an outer surface of the valve component, where the inner skirt may be sutured to at least the inflow tract of the valve component and to an inner surface of the stent. An outer skirt may also be provided that is sutured onto an outer surface of the stent.

Some embodiments of the present disclosure provide a cardiac stent-valve delivery system that includes an inner assembly and an outer assembly. The inner assembly may include a guide wire lumen (e.g., polymeric tubing) and a stent holder for removable attachment to a stent-valve. The outer assembly may include a sheath. The inner member and the outer member may be co-axially positioned and slidable relative to one another in order to transition from a closed position to an open position, such that in the closed position the sheath encompasses the stent-valve still attached to the stent holder and thus constrains expansion of the stent-valve. In the open position, the outer sheath may not constrain expansion of the stent-valve and thus the stent-valve may detach from the stent holder and expand to a fully expanded configuration.

In some embodiments, the inner assembly of the delivery device may include a radioopaque marker band or fluoroscopic marker fixed to the guide wire lumen distal of the stent holder.

In some embodiments, the diameter of the outer assembly of the delivery device varies over its longitudinal axis.

In some embodiments of the present disclosure, a method is provided for replacing an aortic valve within a human body. A stent-valve may be covered with a sheath in order to maintain the stent-valve in a collapsed configuration. The stent-valve may then may be inserted in the collapsed configuration into the human body without contacting the ascending aorta or aortic arch. The stent-valve may be partially expanded by sliding the sheath towards the left ventricle of the heart. This sliding of the sheath towards the left ventricle may cause expansion of a distal end of the stent-valve while the proximal end of the stent-valve remains constrained by the sheath. The sheath may be further slid towards the left ventricle of the heart in order to cause full expansion of the stent-valve. In some embodiments, the stent-valve may be recaptured prior to its full expansion by sliding the sheath in the opposite direction.

In some embodiments, a method for cardiac valve replacement is provided that includes releasing a distal end of a stent-valve from a sheath, where the distal end includes a radiopaque marker positioned thereon (e.g., radioopaque marker band). The stent-valve is rotated, if necessary, to orient the stent-valve appropriately with respect to the coronary arteries (e.g., to prevent the commissures from facing the coronary arteries). The stabilization arches or loops of the stent-valve are released from the sheath, in order to cause at least one of the stabilization arches to contact the aorta. The upper anchoring crown of the stent-valve is released from the sheath and is brought into contact with the native valve leaflets. A lower anchoring crown of the stent-valve is released from the sheath and brought into contact with an annulus/inflow tract. The lower anchoring crown may be the proximal section of the stent-valve such that releasing the lower anchoring crown causes the stent-valve to be fully released from the sheath of the delivery device.

According to some embodiments, there is provided a system for replacing a valve within a human body comprising: a delivery device; and a replacement valve for use within a human body comprising: a valve component, and a stent component configured to house at least a portion of the valve component comprising a proximal end and a distal end, the stent component further comprising: a lower anchoring crown defining an at least partly conical body, where the lower anchoring crown defines the proximal end of the stent component; an upper anchoring crown in communication with the lower anchoring crown and defining an at least partly conical body, where the conical body of the lower anchoring crown slopes outwardly in the direction of the proximal end, and the conical body of the upper anchoring crown slopes outwardly in the direction of the distal end; the distal stent section defines an at least partly conical body, where the distal stent section comprises a conical commissural post section and stabilization arch section, where the commissural post section is in communication with the upper anchoring crown; and the stabilization arch section is in communication with commissural post section and defines an at least partly conical body, where the stabilization arch section defines the distal end. The stabilization arch may slope outwardly from the commissural post and/or turn inwardly at its apex remote from the commissural post. The stent component may have a central, longitudinal axis and comprising at least one attachment element for removable attachment to a delivery device, where the at least one attachment element is located at a proximal end of the stent component, where the proximal end is defined as the end toward the left ventricle when delivered from a transapical approach.

In some embodiments the (at least one) attachment element is formed generally in the form of an opening which is able to enlarge when the stent component radially expands. The opening is adapted to receive a pin arranged on the stent holder.

In particular the attachment element may be formed by an axial elongation of at least one cell of the lower crown. Preferably three attachment elements are formed by three such elongated cells, optionally equally spaced around the perimeter. Preferably the or each elongated element is adapted to receive a respective pin arranged, preferably radially, on the stent holder.

In some embodiments, the (at least one) attachment element is formed generally in the shape of a hook.

In particular the attachment element is formed by an elongation of at least one cell of the lower crown which is inwardly inclined and/or bent. Preferably three attachment elements are formed by three such elongated cells, optionally equally spaced around the perimeter of the stent and bent inwardly. The or each inclined attachment element may be adapted to be received by a groove arranged on a stent holder and/or to engage a respective pin arranged on the stent holder.

In some embodiments, the delivery device comprises: an inner member comprising a guide wire lumen and a stent holder; and an outer member comprising a sheath; where the stent holder comprises for example a groove for receiving the attachment element of the stent component and/or at least one pin for engaging an attachment element of the stent element in form of an opening, The pins may be arranged radially to engage axial elongations of the stent element or the pins may subtend an angle smaller than 90 degree with the axis of the stent holder, preferably may be arranged axially, to engage an inwardly inclined or bent attachment element with an opening.

The axial pins may be arranged in a circumferential groove of the stent holder.

Each radial pin may be arranged in a separate axial groove of the stent holder. Preferably there are three grooves equally spaced around the perimeter of the stent holder to receive corresponding attachment elements of the stent.

In some embodiments the stent holder comprises ramp surfaces to facilitate the release of the stent component after removing the sheath from the stent.

Preferably each of the axial grooves comprises ramp surfaces, for example facets on either sides of the groove, to facilitate the lifting of the attachment elements when the stent expands. Especially when the stent component and the stent holder do not remain in exact coaxial relation after removing the sheath from the stent the release of the stent component and the lifting of the attachment elements are ensured.

The inner member and the outer member are co-axially positioned and slidable relative to one another in order to transition from a closed position to an open position, such that in the closed position the sheath encompasses at least a portion of the stent-valve still attached to the stent holder constraining expansion of the stent-valve, and such that in the open position the outer sheath does not constrain expansion of the stent-valve and the stent-valve detaches from the stent holder and expands to an expanded configuration. The release of the stent-valve from the stent holder may optionally be facilitated by slight rotation and/or axial movement of the stent holder relative to the attachment element.

According to some embodiments, there is provided a method for replacing an aortic valve within a human body, the method comprising: covering the replacement valves of the present invention with a sheath in order to maintain the replacement valve in a collapsed configuration; transapically inserting the replacement valve still in the collapsed configuration into the human body; partially expanding the replacement valve by sliding the sheath towards the left ventricle of the heart, wherein said sliding of the sheath towards the left ventricle causes expansion of a distal end of the replacement valve while the proximal end of the replacement valve remains constrained by the sheath; and further sliding the sheath towards the left ventricle of the heart in order to substantially release the entire replacement valve such that the replacement valve is allowed to expand to an expanded configuration.

In some embodiments, the method may comprise sliding the sheath in the opposite direction prior to said full expansion in order to recapture the replacement valve within the sheath.

According to some embodiments, there is provided a method for cardiac valve replacement comprising: releasing a distal end of the replacement valves of the present invention from a sheath, wherein the distal end comprises a radiopaque marker; rotating the replacement valve, if necessary, to orient the replacement valve appropriately with respect to the coronary arteries; releasing arches of the replacement valve from the sheath, in order to cause at least one of the arches to contact the aorta; releasing a first conical crown of the replacement valve from the sheath, in order to cause the first conical crown to contact native valve leaflets; and releasing a second crown of the replacement valve from the sheath, in order to cause the second crown to contact an annulus/inflow tract, wherein the second crown comprises the proximal section of the replacement valve and said releasing of the second crown comprises fully releasing the replacement valve from the sheath.

According to some embodiments, there is provided a method for cardiac valve replacement comprising: releasing a distal end of the replacement valves of the present invention from a sheath, wherein the distal end comprises a radiopaque marker and a plurality of arches; rotating the replacement valve, if necessary, to orient the replacement valve appropriately with respect to the coronary arteries; releasing the arches of the replacement valve from the sheath, in order to urge the arches towards (and optionally contacting) an area above a native valve; releasing a first conical crown portion of the replacement valve from the sheath, in order to cause the first conical crown to contact the native valve leaflets; and releasing a second crown portion of the replacement valve from the sheath, in order to cause the second crown to contact an annulus/inflow tract of the native valve, wherein the second crown is the proximal section of the replacement valve and said releasing the second crown comprises fully releasing the replacement valve from the sheath.

According to some embodiments, there is provided a method for replacing a worn or diseased valve comprising: transapically implanting the replacement valves of the present invention, wherein the replacement valve comprises: a valve component; and a stent component to which the valve component is affixed thereto, the stent component comprising: a longitudinal axis; a lower anchoring crown including a substantially conical shape having a narrow end, a broad end and a predetermined first height; and an upper anchoring crown including a substantially conical shape having a narrow end, a broad end and a predetermined second height, wherein: a center axis of each of the lower anchoring crown and the upper anchoring crown are arranged to align substantially with the longitudinal axis; the narrow ends of the lower anchoring crown and upper anchoring crown are arranged to meet forming an annular groove to receive the annulus of worn or diseased cardiac valve at an implantation site of the heart, the first height of the lower anchoring crown is greater than the second height of the upper anchoring crown; and positioning the replacement valve so that the annular groove receives the annulus of the worn or diseased cardiac valve.

BRIEF DESCRIPTION OF THE DRAWINGS

For a better understanding of the embodiments of the present disclosure, reference is made to the following description, taken in conjunction with the accompanying drawings, in which like reference characters refer to like parts throughout, and in which:

FIGS. 2A to 21 show the size and shape of the elements of the stent component in the expanded and non-expanded configuration according to some embodiments of the disclosure.

FIG. 3 illustrates the anatomical match between the stent and the aortic root.

FIG. 4 illustrates the range of the possible location for the coronary ostia (shaded area).

FIG. 7 shows a bioprosthetic conduit assembled to the metallic stent, aligning the prosthetic commissures to the commissural totem 2 of the stent and keeping the outflow free edge of the prosthesis above the outward curvature of the upper anchoring crown 3, in order to avoid the reduction of the orifice area of the prosthesis.

FIG. 8 shows a porcine pericardium strip covers the free edge of the valve outflow tract.

FIG. 9 illustrates a placement of a double polyester (PET) fabric skirt relative to a stent component, according to some embodiments of the present disclosure.

FIG. 10 shows a delivery system for distal-to-proximal expansion of a stent-valve, according to some embodiments of the present disclosure.

FIG. 11 shows elements of the delivery system for distal-to-proximal expansion of a stent-valve, according to some embodiments of the present disclosure.

FIG. 12 shows elements of the delivery system for distal-to-proximal expansion of a stent-valve, according to some embodiments of the present disclosure.

FIG. 13 shows the partial release of an aortic bioprosthesis or stented replacement valve 100 according to some embodiments.

FIG. 14 shows the full release of an aortic bioprosthesis or stented replacement valve 100 according to some embodiments.

FIG. 15 shows an example of a recapture control knob 575 of the delivery device.

FIG. 16 shows a delivery system for distal-to-proximal expansion of a stent-valve with a low-profile tip 555, according to some embodiments of the present disclosure.

FIG. 17 shows a stent holder to be arranged on a delivery system.

DETAILED DESCRIPTION

Figure 1:
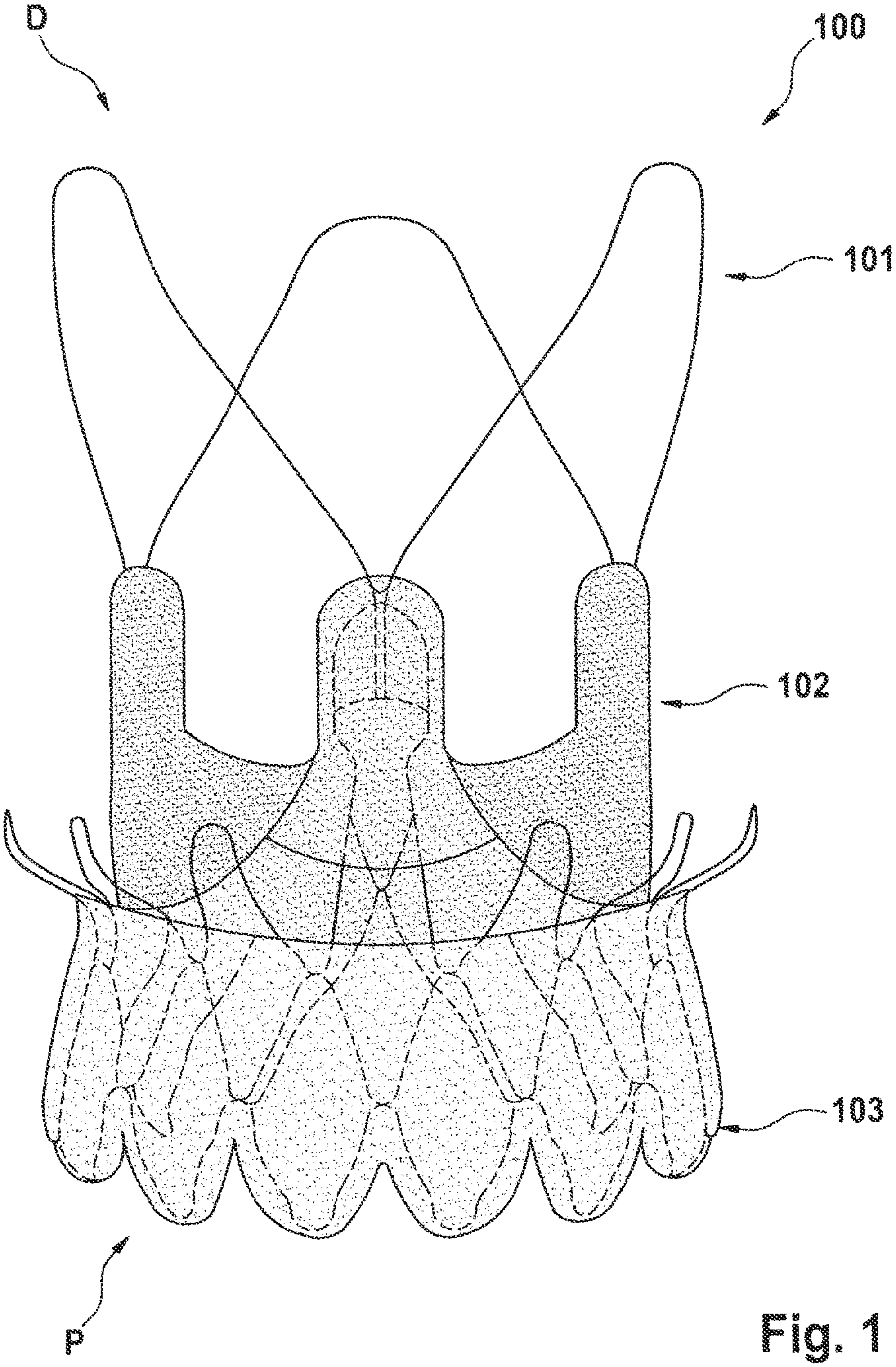
FIG. 1 shows the placement of a double polyester (PET) fabric skirt 103 relative to a stent component 101, as well as placement of a valve-component within the stent 102.

Some embodiments of the present disclosure are directed to systems, methods, and devices for cardiac valve replacement. For example, such methods, systems, and devices may be applicable to the full range of cardiac-valve therapies including, for example, replacement of failed aortic, mitral, tricuspid, and pulmonary valves. Some embodiments may facilitate a surgical approach on a beating heart without the need for an open-chest cavity and heart-lung bypass. This minimally-invasive surgical approach may reduce the risks associated with replacing a failed native valve in the first instance, as well as the risks associated with secondary or subsequent surgeries to replace failed artificial (e.g., biological or synthetic) valves.

Stents, Stent-ValvesNalved-Stents Some embodiments of the present disclosure relate to stents and stent-valves or valved-stents. Valved-stents according to some embodiments of the present disclosure may include a valve component and at least one stent component (e.g., a single-stent-valve or a double-stent-valve). The valve component may include a biological valve (e.g., porcine or bovine harvested valve), a synthetic valve (e.g., synthetic valve leaflet made of biological tissue (e.g., pericardium), and/or synthetic valve leaflet material and/or a mechanical valve assembly), any other suitable material(s). The stent and valve components according to some embodiments may be capable of at least two configurations: a collapsed or contracted configuration (e.g., during delivery) and an expanded configuration (e.g., after implantation).

According to some embodiments, the valved-stent or stent-valves of the present disclosure may be used as replacement heart valves and may be used in methods for replacing diseased or damaged heart valves. Heart valves are passive structures that simply open and close in response to differential pressures on either side of the particular valve. Heart valve comprise moveable "leaflets" that open and close in response to differential pressures on either side of the valve's leaflets. The mitral valve has two leaflets and the tricuspid valve has three. The aortic and pulmonary valves are referred to as "semilunar valves" due to the unique appearance of their leaflets or "cusps" and are shaped somewhat like a half-moon. The aortic and pulmonary valves each have three cusps.

The valve component may be designed to be flexible, compressible, host-compatible, and non-thrombogenic. The valve component can be made from various materials, for example, fresh, cryopreserved or glutaraldehyde fixed allografts or xenografts. Synthetic biocompatible materials such as polytetrafluoroethylene, polyester, polyurethane, nitinol or other alloy/metal foil sheet material and the like may be used. The preferred material for the valve component is mammal pericardium tissue, particularly juvenile-age animal pericardium tissue.

The valve component can be any replacement heart valve known or used as cardiac replacement valves. Replacement heart valves are generally categorized into one of three categories: artificial mechanical valves; transplanted valves; and tissue valves. Mechanical valves are typically constructed from nonbiological materials such as plastics, metals, and other artificial materials. Transplanted valves are natural valves taken from cadavers. These valves are typically removed and frozen in liquid nitrogen, and are stored for later use. They are typically fixed in glutaraldehyde to eliminate antigenicity. Artificial tissue valves are valves constructed from animal tissue, such as bovine or porcine tissue. Efforts have also been made at using tissue from the patient for which the valve will be constructed. Such regenerative valves may also be used in combination with the stent components described herein. The choice of which type of replacement heart valves are generally based on the following considerations: hemodynamic performance, thrombogenicity, durability, and ease of surgical implantation.

Most tissue valves are constructed by sewing the leaflets of pig aortic valves to a stent to hold the leaflets in proper position, or by constructing valve leaflets from the pericardial sac of cows or pigs and sewing them to a stent. See e.g., U.S. Patent Publication No. 2005/01 13910, the disclosure of which is herein incorporated by reference in its entirety. Methods of creating artificial tissue valves is described in U.S. Pat. Nos. 5,163,955, 5,571,174, and 5,653,749, the disclosures of which are herein incorporated by reference in their entireties.

According to some embodiments, the valve component is attached to the inner channel (also referred to as lumen) of the stent member. This may be accomplished using any means known in the art. The valve component may be attached to the inner channel of the stent member by suture or stitch, for example, by suturing the outer surface of the valve component pericardium material to the stent member, and for example, attaching the valve component to the commissural posts 2 of the stent member. The attachment position of the valve may be closer to the proximal end of the stent chosen with the understanding that the annulus of the native valve being replaced will preferably engage the outer surface of the stent at the groove by the upper anchoring crown 3.

FIG. 1 illustrates an aortic bioprosthesis or stented replacement valve 100 according to some embodiments. The stent component 101 supports a replacement biological valve prosthesis 102. In some embodiments, the stent-valve comprises the following elements: a valve 102 (e.g., biologic porcine valve) which regulates the blood flow between the left ventricle and the aorta; a self expandable Nitinol stent 101 acting as an anchoring structure within the native aortic annulus for the biological valve which is sutured on; and a double skirt 103 (e.g., double polyester (PET) skirts) sutured on the inner and outer surface of the stent to reinforce the biological porcine valve and facilitate the leak-tightness of the implant.

The stent 101 of the replacement valve may be self-expanding being formed from a suitable shape memory or superelastic material or combination of materials (e.g., nitinol). The stent is manufactured according to any know method in the art. In some embodiments, the stent is manufactured by laser cutting a tube or single sheet of material (e.g., nitinol). For example, the stent may be cut from a tube and then step-by-step expanded up to its final diameter by heat treatment on a mandrel. In some embodiments, the stent is manufactured by laser cutting from a tube of suitable shape memory or superelastic material or combination of materials (e.g., nitinol). Heat forming treatments may be applied, according to the current state-of-art, in order to fix the final shape of the stent. As another example, the stent may be cut from a single sheet of material, and then subsequently rolled and welded to the desired diameter.

FIG. 2 illustrates the stent component of a aortic bioprosthesis or stented replacement valve 100 according to some embodiments. The stent component 101 defines a first (e.g., proximal) end and a second (e.g., distal) end and may be described as having one or more of 5 predominant features or sections that include: stabilization arches 1; commissural posts 2; upper (first) anchoring crown 3; lower (second) anchoring crown/portion 4; and inflow hooks 5.

Viewed alternatively, the stent component 101 may be described as having one or more of: a distal stent section defining the distal end; a proximal anchoring section defining the proximal end; and an upper (first) crown section. The distal stent section may comprise the stabilization arch (section) 1 and commissural post (section) 2. The proximal anchoring section may comprise the lower (second) anchoring crown/portion 4. The upper (first) crown section may comprise the upper anchoring crown 3. The upper crown section may comprise a first divergent portion that diverges outwardly in a direction towards the distal end. The first crown section may have a free end. The free end may be proximal of the distal end of the stent and/or distal of the proximal end of the stent.

The stabilization arches 1 define the outflow section of the stent component (relative to main bloodflow direction in the native valve), and include a generally divergent (e.g., conical) shape, with the conical curvature oriented in generally the same direction as the curvature of the upper anchoring crown 3. In some embodiments, the stabilization arches 1 include a plurality of (e.g., 2, 3, 4, 5, 6, or more) larger arches generally in referred position to the arches in the commissural posts 2. In some embodiments, these larger arches are the first components of the stent to be deployed during the distal-to-proximal release of the aortic bioprosthesis or stented replacement valve 100 from a first, unexpended configuration to a second, expanded configuration (See e.g., FIGS. 13 and 14).

In some embodiments, at least one of the deployed arches 1 engages the ascending aorta thereby orientating the delivery system/stent-valve longitudinally within the aorta/aortic annulus, thus preventing any tilting of the implanted stent-valve 100. The stent 101 may also include a radiopaque marker on or close to the distal end of one of the arches to aid in tracking the placement of the stent during implantation.

The radial force of the stabilization arches 1 may be increased by adjusting the length and angle of the stabilization arches 1. In some embodiments, the tip of the elements forming the upper anchoring crown 3 and/or the stabilization arches 1 may be bent towards the longitudinal axis of the stent thereby avoiding potential injury of the sinus of vasalva (see e.g., FIG. 2). The free area between the stabilization arches 1 may be adjusted (i.e., increased or decreased) to improve the blood flow to the coronary arteries. This section of the stent may be attached to the anchoring crown section.

The commissural posts 2 are the portion of the stent to which the valve prosthesis 102 is attached. In some embodiment, commissural posts 2 includes a plurality (e.g., 2, 3, 4, 5, 6, or more) of arches (or other type of structure, e.g., post) for the fixation of the prosthetic valve commissures. In some embodiments, the commissural posts 2 may be designed with an asymmetrical shape (not shown), in order to easily identify under fluoroscopy, the three-dimensional position of each prosthetic commissure. In some embodiments, the commissural posts 2 may be designed with dot markerbands to identify their respective position with regard to the ostium of the coronary arteries.

The upper anchoring crown 3 section may include a generally divergent portion. The divergent portion may have any suitable shape, such as conical, or flared with a non-uniform angle of divergence with respect to the central axis (e.g. domelike or trumpet-mouth) giving a convex or concave divergence, or a combination of any of these. The conical/divergent angle or curvature may be oriented in the opposite direction to the angle or curvature of lower anchoring crown 4 or proximal anchoring stent section 4. Due to its geometry, upper anchoring crown 3 creates a form fit with the supra-valvular apparatus and the native leaflets of the aortic valve. Therefore it prevents the migration of the stent-valve towards the left ventricle (migration of the implant during diastole). Furthermore, the upper anchoring crown 3 provides a radial force that creates an additional friction fit against the aortic annulus plus native leaflets. In some embodiments, the tips of crown elements 3 may be bent to form a cylindrical surface, thus reducing risks of sinus perforation.

Due to its geometry, the lower anchoring crown 4 section creates a form fitting with the inflow of an aortic valve (for example) and therefore prevents migration of the prosthesis towards the ascending aorta (migration of the implant towards the ascending aorta during systole). This section defines the proximal end P of the stent component (relative to a native valve, or heart or ventricle). The section is generally conically shaped. In some embodiments, the inflow edge may be bended inward to avoid injuries at the level of the sub-valvular apparatus. Furthermore, the lower anchoring crown 4 provides a radial force that creates an additional friction fit against the inflow tract/aortic annulus.

Some embodiments may further include inflow-edge hooks 5, which assists the fixation of the aortic bioprosthesis to the delivery system (thru the stent holder) during the release procedure.

In some embodiments, the anchoring of the aortic bioprosthesis or stented replacement valve 100 within the native calcified aortic annulus relies on two different aspects: form fitting based on the shape and features of the stent (e.g., by the joined shape of section 3 and section 4); and friction fitting based on the radial force applied by the self-expandable stent. The anatomical match between the stent and the aortic root is illustrated in FIG. 3.

Figure 3:
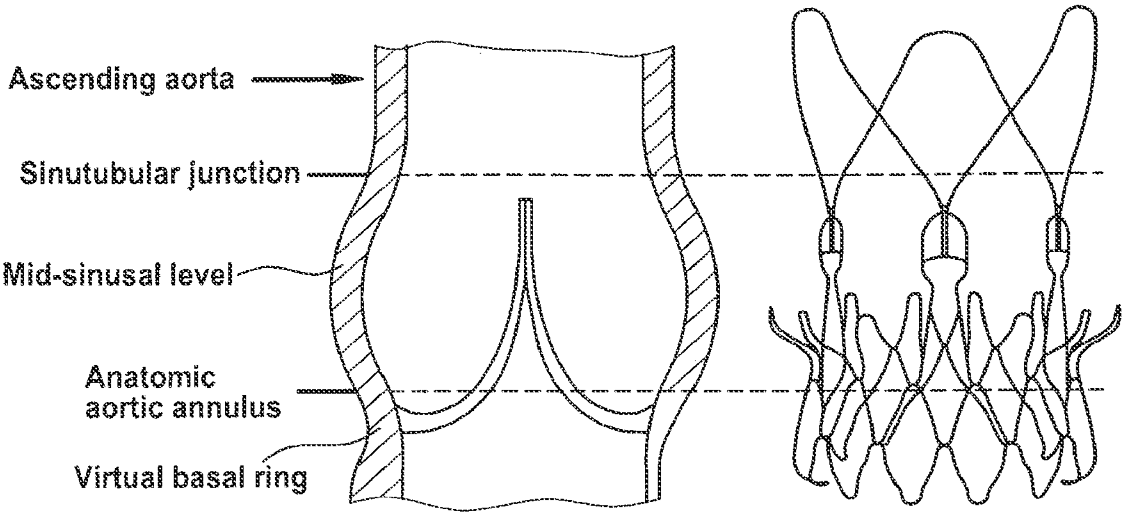

In some embodiments the tips of the upper anchoring crown may rest in a final position between the sinutubular junction and the aortic annulus according to FIG. 3 and press on the pushed back native valve leaflets.

Figure 4:
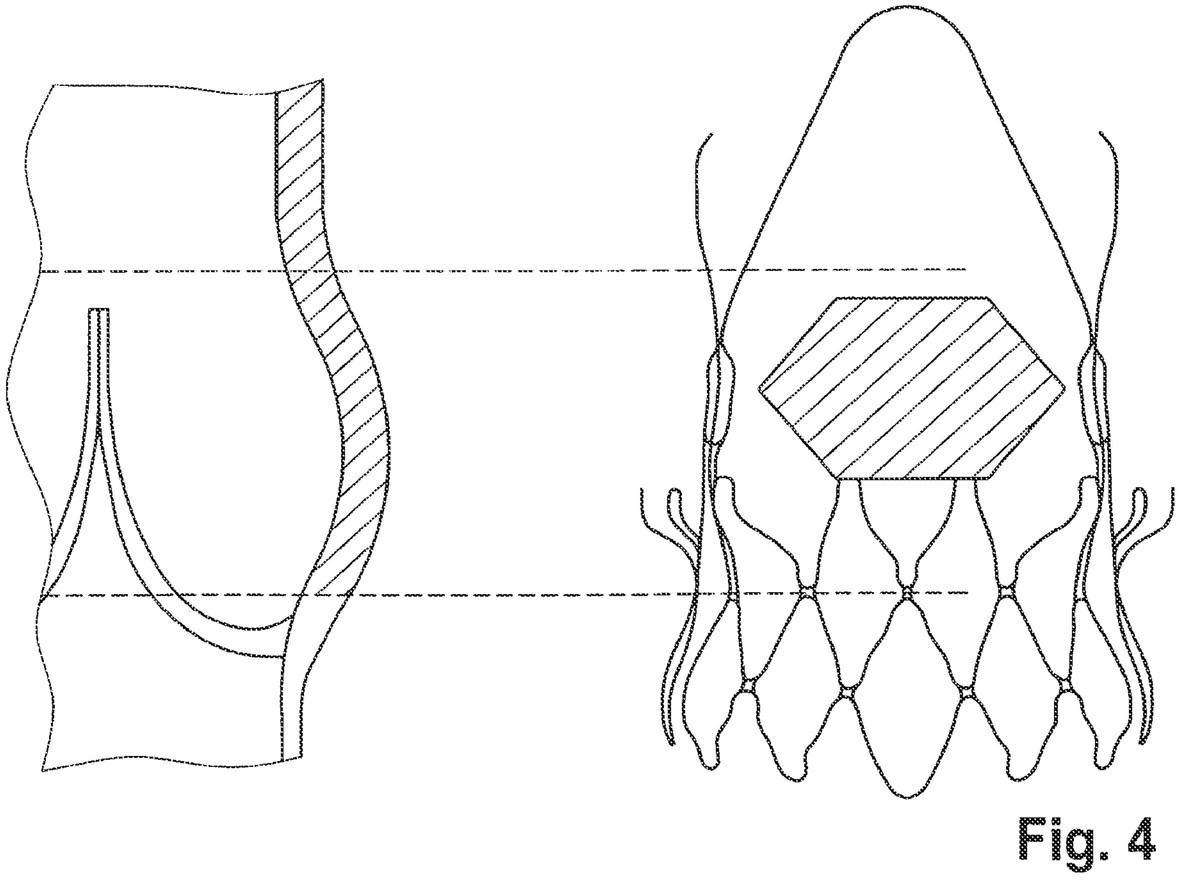

The shaded box in FIG. 4 indicates the range of the possible location for the coronary ostia. The large openings in between the commissural totems 2 and the arches reduce the risk of coronary flow impairment. In addition, the frame of the stent does not interfere with the possible need of catheterizing the coronaries.

Figure 5A:
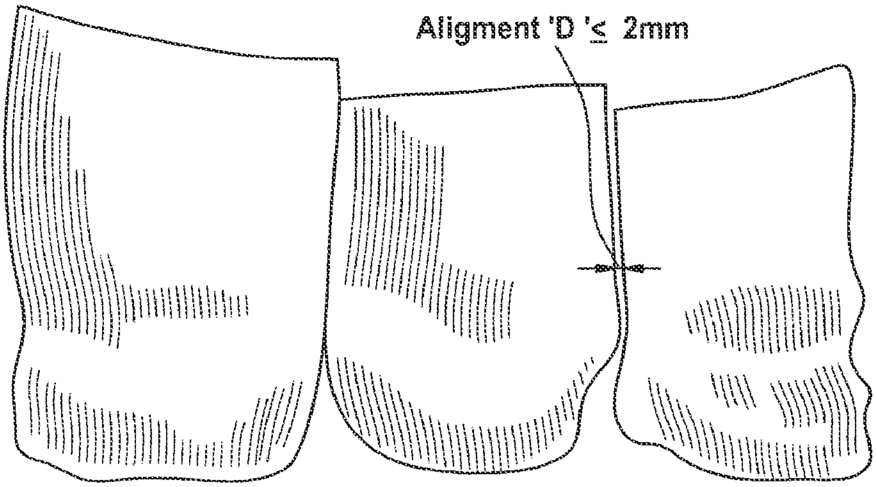
FIGS. 5A and 5B and FIGS. 6A and 6B illustrate the process of selecting and suturing together three Non-Coronary porcine cusps (FIGS. 5A and B). The biological conduit obtained in this way is trimmed, such as trimmed above the line of insertion of the leaflets. An inner PET-tube is positioned on the outer surface of the biologic porcine valve and trimmed according to the shape of the biological conduit. The two parts are then sutured together along the free edges (FIGS. 6A and B).
Figure 5B:
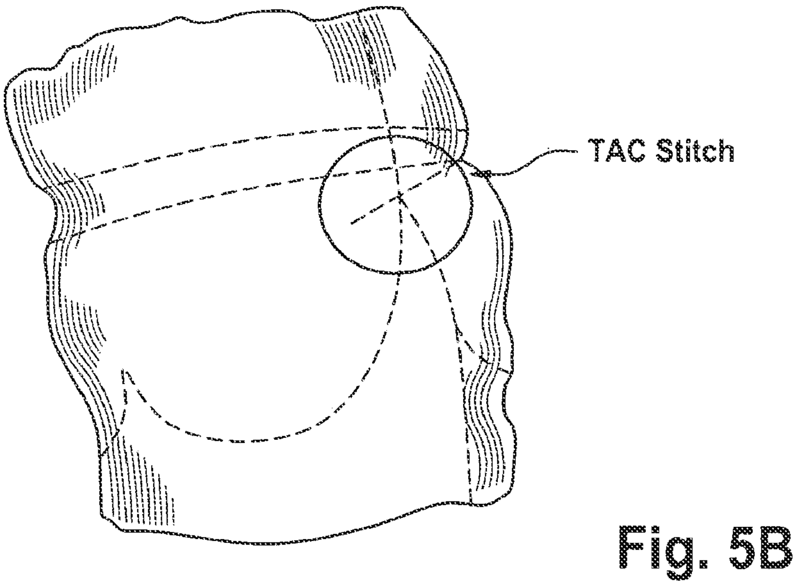
Figure 6A:
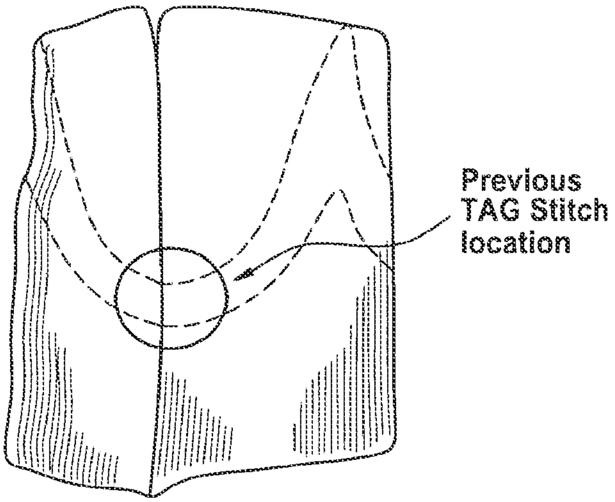
Figure 6B:
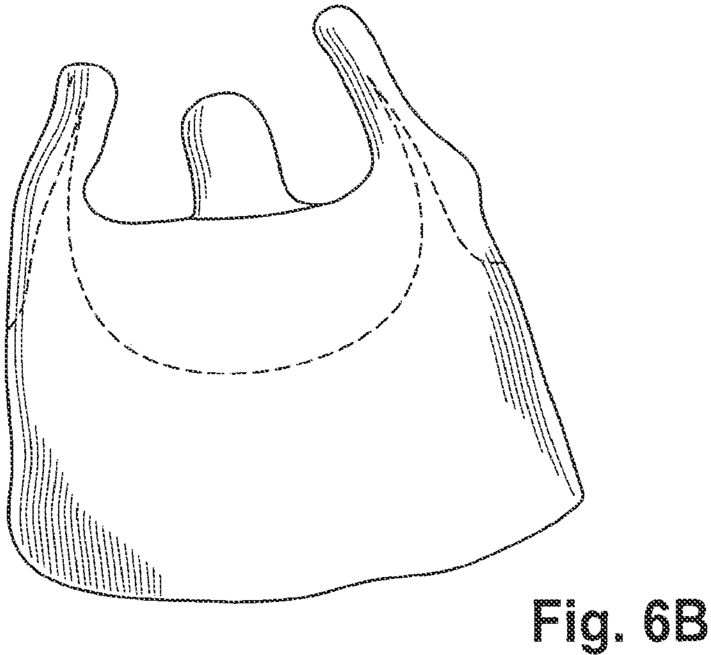

In some embodiments, the aortic bioprosthesis or stented replacement valve 100 comprises a biological component, which may be obtained by selecting and suturing together three Non-Coronary porcine cusps (see e.g., FIGS. 5A and B). The biological conduit obtained in this way is trimmed, such as trimmed above the line of insertion of the leaflets (e.g., removal of the Valsava sinuses). An inner PET-tube may be positioned on the outer surface of the biologic porcine valve and trimmed according to the shape of the biological conduit. The two parts may then be sutured together along the free edges (see FIGS. 6A and B). A manufacturing process related to the assembling of the biological component is disclosed in U.S. Provisional Application No. 61/109,310 and related PCT application WO 2010/049160, the entire contents of which are incorporated herein by reference it their entireties.

Figure 7:
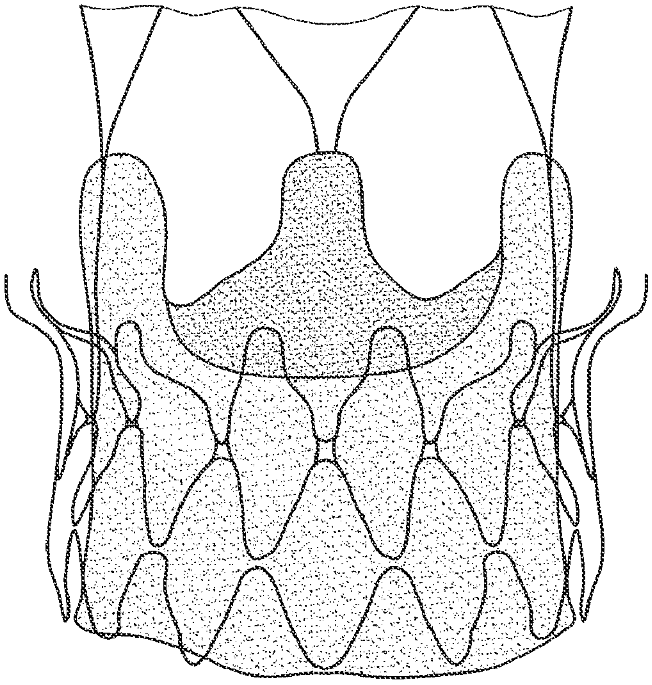

In some embodiments, the bioprosthetic conduit is assembled to the metallic stent, aligning the prosthetic commissures to the commissural totem 2 of the stent and keeping the outflow free edge of the prosthesis above the outward curvature of the upper anchoring crown 3, in order to avoid the reduction of the orifice area of the prosthesis (see FIG. 7).

Figure 8:
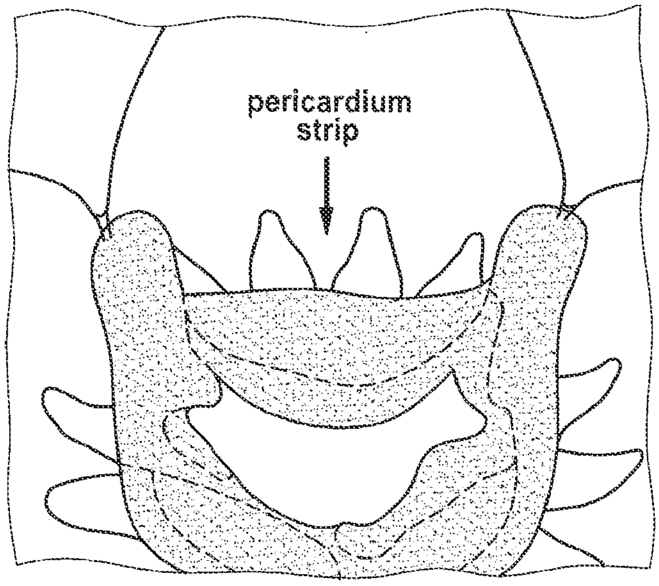

In some embodiments, an additional porcine pericardium strip covers the free edge of the valve outflow tract (FIG. 8). The inner PET-skirt reinforces the biological tissue in the area where stitches fix the valve to the stent struts. The pericardium strip protects the valve leaflets from direct contact with the stitches of the finishing hem at the distal hedge of the valve.

In some embodiments, the outer PET-skirt sutured on the lower anchoring crown contributes to mitigate the risk of paravalvular leakage of the implant. The skirt 103 (see FIG. 1) is designed to cover the lattice structure or framework of the stent component. In some embodiments, the skirt follows the lattice structure of the lower anchoring crown of the stent component and may be described as a specific atraumatic "flower" design (see, for example, FIG. 9). The design of the skirt 103 creates a geometrical discontinuity at the inflow edge of the outer fabric skirt. In this way, when the stent is reduced in diameter, due to the oversizing of the prosthesis in respect to annulus/LVOT diameter, the fabric shrinkage doesn't create folds. Further, the skirt reduces risk of sharp edges in the framework of the stent that may jeopardize the integrity of the surrounding biological structures (e.g., mitral anterior leaflet, left bundle branch, etc.). The protruding "petals" of the skirt 103 act as soft, dampening elements when bent over the tip of the element forming the lower anchoring crown.

In some embodiments, the overall stent length may be sufficiently small so as to avoid conflict with, for example, the mitral valve when the stent is being used for aortic valve replacement. Of course, it will be understood that these dimensions will vary depending on, for example, the type of valve used and the dimensions given above are included as examples only and other sizes/ranges are available which conform to the present disclosure.

In still other embodiments of the present disclosure, a replacement valve for use within a human body is provided that includes a valve component, a stent component for housing the valve component, and at least two skirts (e.g., polyester (PET) skirts). An inner skirt may be provided that covers at least a portion (e.g., all) of an outer surface of the valve component, where the inner skirt may be sutured to at least the inflow tract of the valve component and to an inner surface of the stent. An outer skirt may also be provided that is sutured onto an outer surface of the stent.

Figure 9:
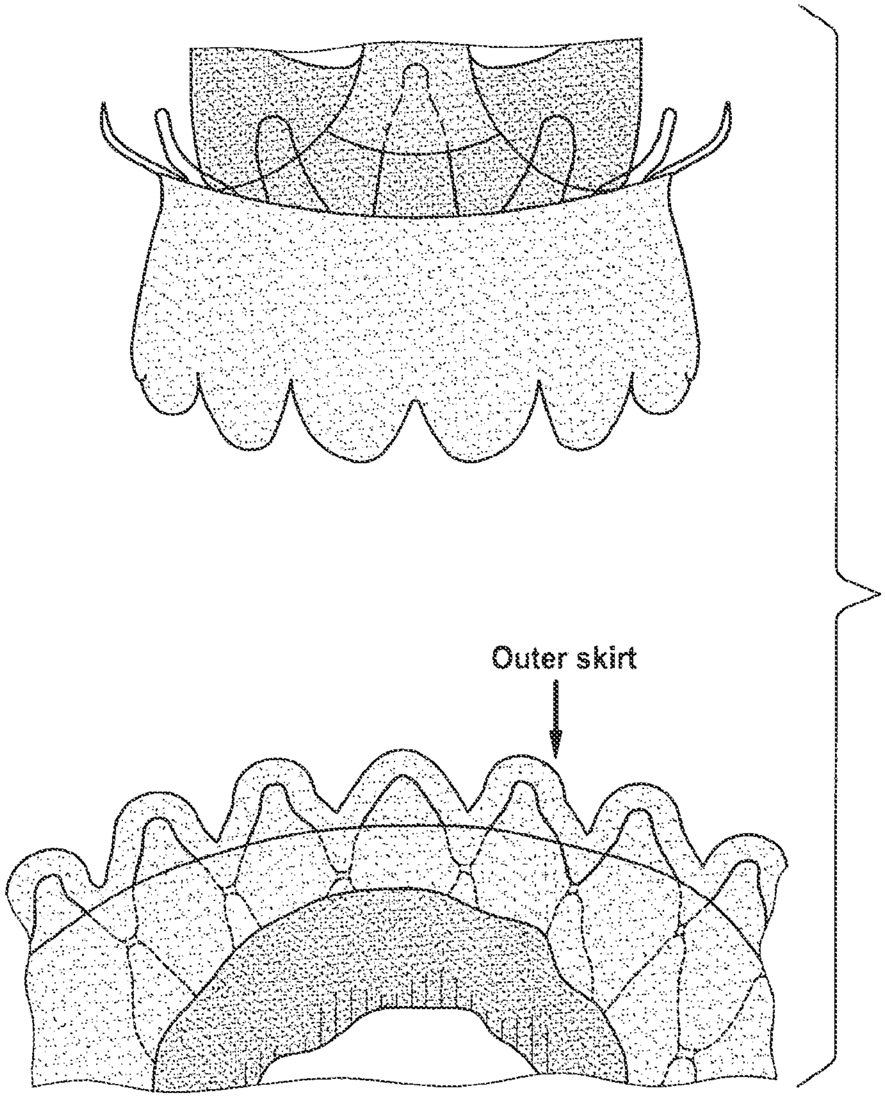

An outer PET fabric skirt may be provided in which the free edge of the stent is covered to avoid injuries of the left ventricle wall and mitral valve (see e.g., FIG. 9).

In some embodiments, a stent is presented which includes a section for commissural valve fixation which is composed of a plurality (e.g., two, three, four, five, six, eight, etc.) longitudinal elements connected on one side to a conically shaped section (for example) used for anchoring towards the left ventricle and on the other side to the conically shaped section (for example) used for stabilization.

According to some embodiments, the stent is designed to better match the size and shape of a biological valve with narrow commissural posts 2 and, in some embodiments, allow a more robust suturing of the valve commissural posts to the stent. Narrow commissural posts 2 according to some embodiments may improve the perfusion of the coronary arteries via the sinus of vasalva. To reduce the deflection of the longitudinal elements under diastolic pressure, an additional reinforcement crown may be added as well in some embodiments.

According to some embodiments, the stent design allowing for the fixation of the valve commissural posts 2, according to some embodiments, provides a further advantage, as the size and shape of such stents preferably does not change substantially, and does not change during a required crimping process for loading the stent (with valve, "valved-stent") onto a delivery device. Accordingly, this may reduce (and preferably does reduce) the risks of suture damage and facilitating crimping and subsequently releasing of the valved-stent (for example).

Although a number of embodiments are herein described, other modifications are possible, and thus, the noted embodiments are for illustrative purposes only.

Figure 2A:
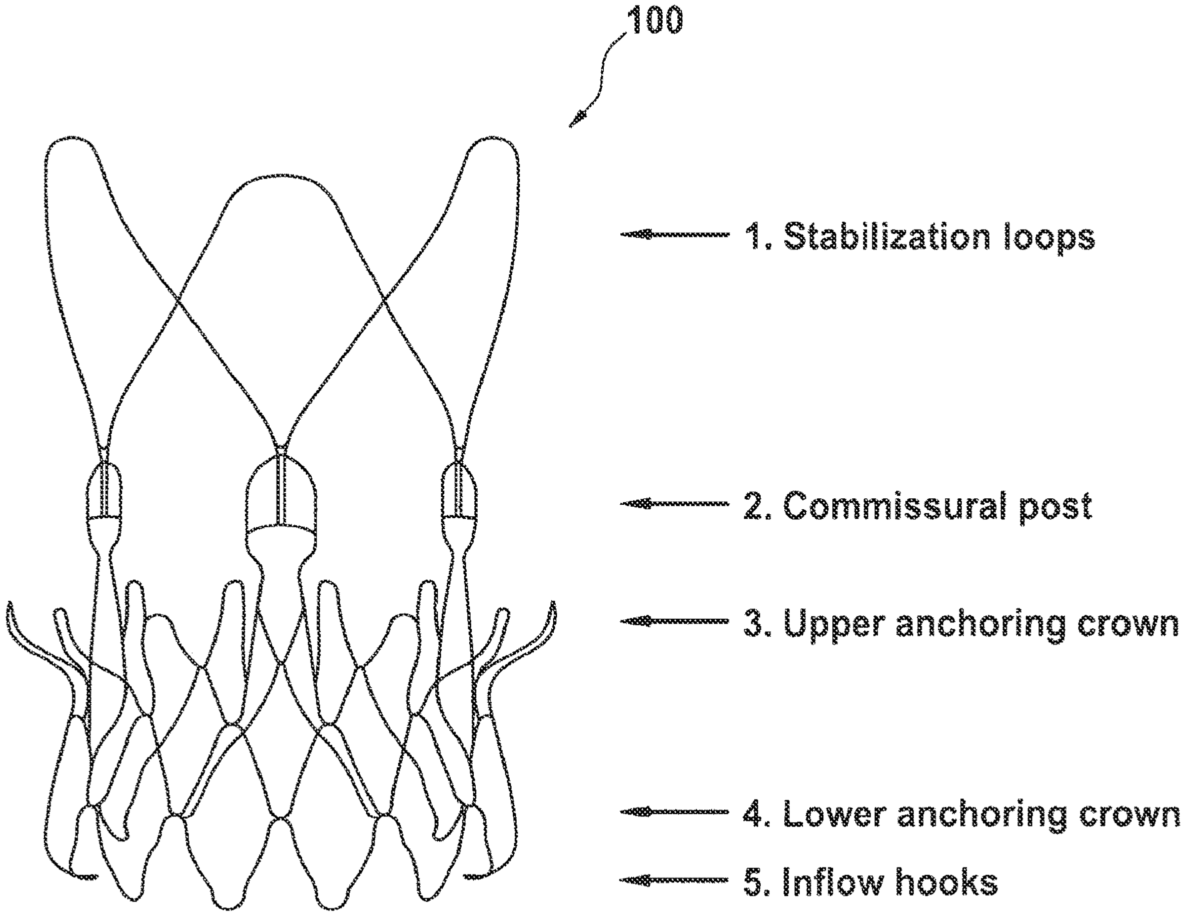
Figure 2B:
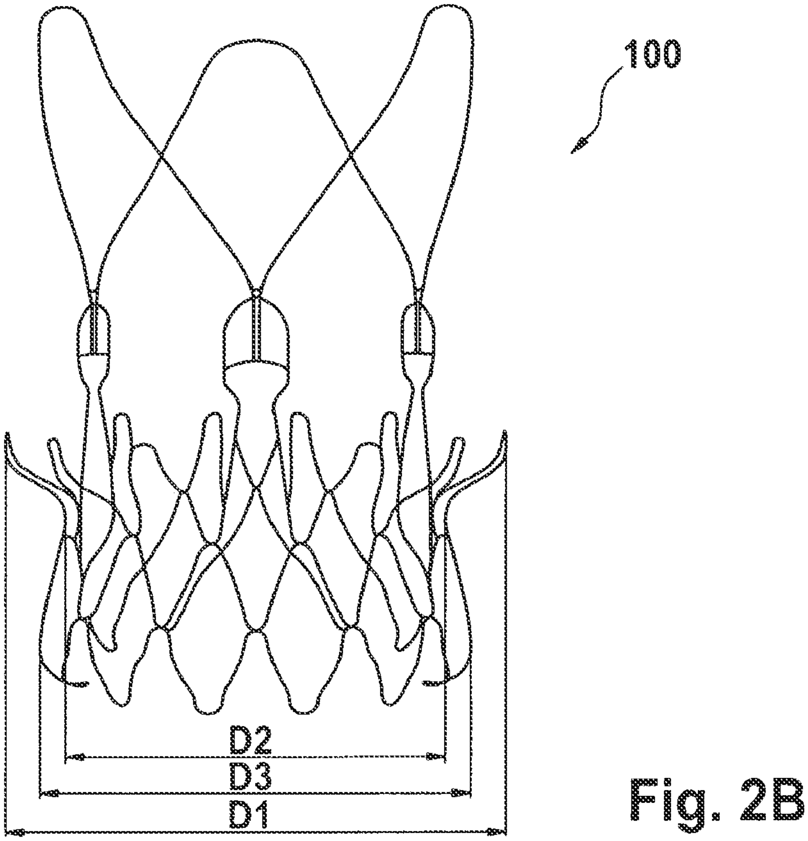
Figure 2C:
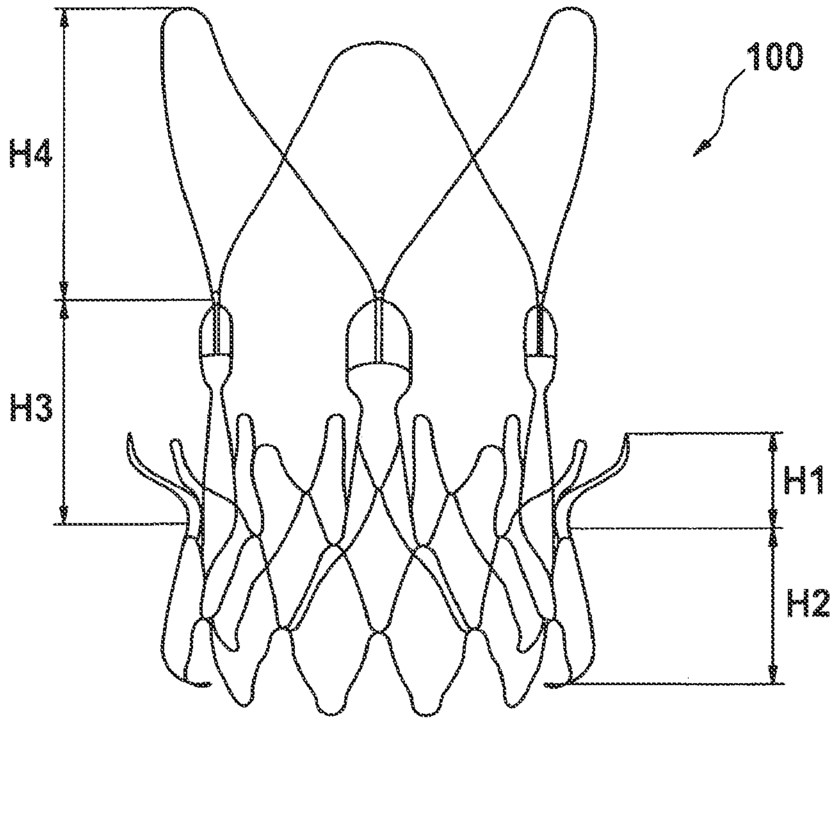
Figure 2D:
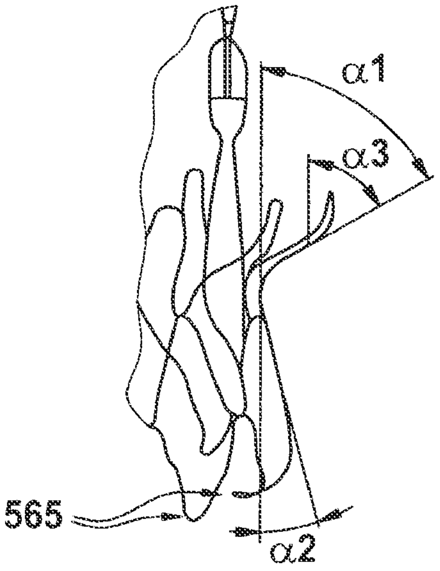

FIGS. 2B to 2D are provided to illustrate the dimensions of the stent component. D3 represents the diameter of the most proximal edge of the stent component in the expanded configuration. D2 represents the diameter of the stent component at the juncture between the upper and lower anchoring crowns. H2 represents the axial distance between the planes of the diameters D2 and D3 in the expanded configuration. D1 represents the diameter of the most distal edge of the upper anchoring crown of the stent component in the expanded configuration. H1 represents the axial distance between the planes of the diameters D1 and D2 in the expanded configuration.

The length of H2 may be between about 3 to about 15 mm (e.g., about 3 mm, about 4 mm, about 5 mm, about 6 mm, about 7 mm, about 8 mm, about 9 mm, about 10 mm, about 11 mm, about 12 mm, about 13 mm, about 14 mm, and about 15 mm). The length of H2 may been adjusted depending on the intended application of the stent of stent-valve. For example, the length of H2 may range from about 3 to about 5 mm, about 3 to about 7 mm, about 3 to about 12 mm, about 3 to about 15 mm, about 3 to about 20 mm, about 5 to about 10 mm, about 5 to about 12 mm, about 5 to about 15 mm, about 7 to about 10 mm, about 7 to about 12 mm, about 7 to about 15 mm, about 10 to about 13 mm, about 10 to about 15 mm, or about 7 to about 20 mm. For example, the length of this section may be on the smaller end of the scale to avoid potential conflict with a cardiac valve, such as the mitral valve.

The diameter at D3 may be between about 22 mm to about 40 mm (e.g., about 22 mm, about 23 mm, about 24 mm, about 25 mm, about 26 mm, about 27 mm, about 28 mm, about 29 mm, about 30 mm, about 31 mm, about 32 mm, about 33 mm, about 34 mm, about 35 mm, about 36 mm, about 37 mm, about 38 mm, about 39 mm, and about 40 mm). This diameter D3 may been adjusted depending on the intended application of the stent of stent-valve. Thus, the diameter D3 in the expanded configuration may be from between about 15 mm to about 50 mm, from between about 15 mm to about 40 mm, from between about 20 mm to about 40 mm, from between about 24 mm to about 40 mm, from between about 26 mm to about 40 mm, from between about 28 mm to about 40 mm, from between about 30 mm to about 40 mm, from between about 32 mm to about 40 mm, from between about 34 mm to about 40 mm, from between about 36 mm to about 40 mm, from between about 38 mm to about 40 mm, from between about 22 mm to about 38 mm, from between about 22 mm to about 36 mm, from between about 22 mm to about 34 mm, from between about 22 mm to about 32 mm, from between about 22 mm to about 30 mm, from between about 22 mm to about 28 mm, from between about 24 mm to about 34 mm, from between about 25 mm to about 35 mm, or from between about 25 mm to about 30 mm.

The diameter of the stent component D2 may be between about 20 mm to about 30 mm (e.g., about 20 mm, about 21 mm, about 22 mm, about 23 mm, about 24 mm, about 25 mm, about 26 mm, about 27 mm, about 28 mm, about 29 mm, and about 30 mm). This diameter of the stent component D2 may been adjusted depending on the intended application of the stent of stent-valve. For example, this diameter of the stent component D2 may be sized according to the shape of the annulus of the cardiac valve. Thus, the diameter of the stent component D2 may be from between about 15 mm to about 40 mm, from between about 15 mm to about 30 mm, from between about 18 mm to about 35 mm, from between about 22 mm to about 30 mm, from between about 24 mm to about 30 mm, from between about 26 mm to about 30 mm, from between about 28 mm to about 30 mm, from between about 22 mm to about 28 mm, from between about 22 mm to about 26 mm, from between about 20 mm to about 24 mm, from between about 20 mm to about 26 mm, from between about 20 mm to about 28 mm, and from between about 22 mm to about 32 mm.

The diameter D1 may be between about 22 mm to about 40 mm (e.g., about 22 mm, about 23 mm, about 24 mm, about 25 mm, about 26 mm, about 27 mm, about 28 mm, about 29 mm, about 30 mm, about 31 mm, about 32 mm, about 33 mm, 34 mm, 35 mm, 36 mm, 37 mm, about 38 mm, about 39 mm, and about 40 mm). This diameter D1 may been adjusted depending on the intended application of the stent of stent-valve. Thus, the diameter in the expanded configuration D1 may be from between about 15 mm to about 50 mm, from between about 15 mm to about 40 mm, from between about 20 mm to about 40 mm, from between about 24 mm to about 40 mm, from between about 26 mm to about 40 mm, from between about 28 mm to about 40 mm, from between about 30 mm to about 40 mm, from between about 32 mm to about 40 mm, from between about 34 mm to about 40 mm, from between about 36 mm to about 40 mm, from between about 38 mm to about 40 mm, from between about 22 mm to about 38 mm, from between about 22 mm to about 36 mm, from between about 22 mm to about 34 mm, from between about 22 mm to about 32 mm, from between about 22 mm to about 30 mm, from between about 22 mm to about 28 mm, from between about 24 mm to about 34 mm, from between about 25 mm to about 35 mm, or from between about 25 mm to about 30 mm.

The length of H1 is between about 3 to about 10 mm (e.g., about 3 mm, about 4 mm, about 5 mm, about 6 mm, about 7 mm, about 8 mm, about 9 mm, and about 10 mm). The length of H1 may be adjusted depending on the intended application of the stent of stent-valve. For example, the length of H2 may range from about 3 to about 5 mm, about 3 to about 15 mm, about 3 to about 20 mm, about 5 to about 10 mm, about 7 to about 10 mm, about 7 to about 12 mm, about 7 to about 15 mm, about 10 to about 13 mm, about 5 to about 15 mm, about 7 to about 20 mm. For example, the length of this section may be on the smaller end of the scale to avoid potential conflict with the sinus of Valsalva. FIG. 2D is provided to illustrate the angles of the anchoring crowns. The $\alpha 1$ angle defines the angle of the upper anchoring crown of the stent component in the expanded configuration. The $\alpha 2$ angle defines the angle of the lower anchoring crown of the stent component in the expanded configuration. The $\alpha 3$ angle defines the angle of bending of the tip, which is done so as to prevent injuries of sinus.

The 1 angle may be between from about 0 degree to about 90 degree (e.g., about 10 degree, about 15 degree, about 20 degree, about 25 degree, about 30 degree, about 35 degree, about 40 degree, about 45 degree, about 50 degree, about 55 degree, about 60 degree, about 65 degree, about 70 degree, about 75 degree, and about 80 degree). The $\alpha 1$ angle may be between from about 20 degree to about 70 degree, most preferable between from about 30 degree to about 60 degree. According to some embodiments, the $\alpha 1$ angle is between from about 20 degree to about 80 degree, between from about 20 degree to about 60 degree, between from about 20 degree to about 50 degree, between from about 20 degree to about 45 degree, between from about 40 degree to about 60 degree, between from about 45 degree to about 60 degree, between from about 30 degree to about 50 degree, between from about 30 degree to about 45 degree, between from about 30 degree to about 40 degree, or between from about 25 degree to about 45 degree.

The α2 angle may be between from about 0 degree to about 50 degree (e.g., about degree, about 10 degree, about 15 degree, about 20 degree, about 25 degree, about 30 degree, about 35 degree, about 40 degree, about 45 degree, and about 50 degree). The α2 angle may be between from about 10 degree to about 40 degree, most preferable between from about 10 degree to about 30 degree. According to some embodiments, the α2 angle is between from about 5 degree to about 45 degree, between from about 5 degree to about 40 degree, between from about 5 degree to about 30 degree, between from about 5 degree to about 25 degree, between from about 5 degree to about 20 degree, between from about 5 degree to about 15 degree, between from about 10 degree to about 20 degree, between from about 10 degree to about 25 degree, between from about 10 degree to about 30 degree, between from about 10 degree to about 40 degree, between from about 10 degree to about 45 degree, between from about 15 degree to about 40 degree, between from about 15 degree to about 30 degree, between from about 15 degree to about 25 degree, between from about 20 degree to about 45 degree, between from about 20 degree to about 40 degree, or between from about 20 degree to about 30 degree The α3 angle may be between from about 0 degree to about 180 degree (e.g., about 5 degree, about 10 degree, about 15 degree, about 20 degree, about 25 degree, about 30 degree, about 35 degree, about 40 degree, about 45 degree, about 50 degree, about 55 degree, about 60 degree, about 65 degree, about 70 degree, about 75 degree, about 80 degree, about 85 degree, about 90 degree, about 95 degree, about 100 degree, about 105 degree, about 110 degree, about 115 degree, about 120 degree, about 125 degree, about 130 degree, about 135 degree, about 140 degree, about 145 degree, about 150 degree, about 155 degree, about 160 degree, about 165 degree, about 170 degree, about 175 degree, and about 180 degree). According to some embodiments, the α3 angle is between from about 45 degree to about 90 degree, between from about 45 degree to about 180 degree, between from about 60 degree to about 90 degree, between from about 45 degree to about 120 degree, between from about 60 degree to about 120 degree, between from about 90 degree to about 120 degree, between from about 90 degree to about 180 degree, or between from about 120 degree to about 180 degree.

The length of the upper anchoring crown 3 and commissural posts section 2 of the stent component H3 is between about 3 to about 50 mm (e.g., about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 20 mm, about 22 mm, about 24 mm, about 25 mm, about 26 mm, about 28 mm, about 30 mm, about 32 mm, about 34 mm, about 36 mm, about 38 mm, about 40 mm, about 42 mm, about 44 mm, about 45 mm, about 46 mm, about 48 mm, and about 50 mm). The length of H3 may been adjusted depending on the intended application of the stent of stent-valve. For example, the length of H3 may range from about 3 to about 40 mm, about 3 to about 30 mm, about 3 to about 20 mm, about 3 to about 10 mm, about 10 to about 50 mm, about 10 to about 40 mm, about 10 to about 30 mm, about 10 to about 20 mm, about 15 to about 50 mm, about 15 to about 40 mm, about 15 to about 30 mm, about 20 to about 50 mm, about 20 to about 40 mm, about 20 to about 30 mm, about 15 to about 50 mm, about 25 to about 50 mm, about 30 to about 50 mm, about 40 to about 50 mm, about 15 to about 40 mm, about 25 to about 40 mm, or about 30 to about 40 mm.

The length of the stabilization arches 1 of the stent component H4 is between about 5 to about 50 mm (e.g., about 5 mm, about 6 mm, about 7 mm, about 8 mm, about 9 mm, about 10 mm, about 11 mm, about 12 mm, about 13 mm, about 14 mm, about 15 mm, about 20 mm, about 22 mm, about 24 mm, about 25 mm, about 26 mm, about 28 mm, about 30 mm, about 32 mm, about 34 mm, about 36 mm, about 38 mm, about 40 mm, about 42 mm, about 44 mm, about 45 mm, about 46 mm, about 48 mm, and about 50 mm). The length of H4 may been adjusted depending on the intended application of the stent of stent-valve. For example, the length of H4 may range from about 5 to about 40 mm, about 5 to about 30 mm, about 5 to about 20 mm, about 5 to about 10 mm, about 10 to about 50 mm, about 10 to about 40 mm, about 10 to about 30 mm, about 10 to about 20 mm, about 15 to about 50 mm, about 15 to about 40 mm, about 15 to about 30 mm, about 20 to about 50 mm, about 20 to about 40 mm, about 20 to about 30 mm, about 15 to about 50 mm, about 25 to about 50 mm, about 30 to about 50 mm, about 40 to about 50 mm, about 15 to about 40 mm, about 25 to about 40 mm, or about 30 to about 40 mm.

The α4 and α5 angles (see also FIG. 2F) represent the offset angle from a longitudinal axis of the stabilization arches 1 of the stent component in the expanded configuration. If the stabilization arches are directed away from the center of the stent, the α4 angle is used. If or where the stabilization arches are directed toward the center of the stent, the α5 angle is used.

The α4 angle is preferably between from about 0 degree to about 60 degree (e.g., about 5 degree, about 10 degree, about 15 degree, about 20 degree, about 25 degree, about 30 degree, about 35 degree, about 40 degree, about 45 degree, about 50 degree, about 55 degree, and about 60 degree). According to some embodiments, the α4 angle is between from about 20 degree to about 60 degree, between from about 30 degree to about 60 degree, between from about 40 degree to about 60 degree, between from about 45 degree to about 60 degree, between from about 30 degree to about 50 degree, between from about 30 degree to about 45 degree, between from about 20 degree to about 40 degree, or between from about 15 degree to about 45 degree.

The α5 angle is preferably between from about 0 degree to about 20 degree (e.g., about 5 degree, about 10 degree, about 15 degree, and about 20 degree). According to some embodiments, the α5 angle is between from about 5 degree to about 20 degree, between from about 10 degree to about 20 degree, between from about 15 degree to about 20 degree, between from about 0 degree to about 15 degree, between from about 0 degree to about 10 degree, between from about 5 degree to about 15 degree, between from about 10 degree to about 15 degree, or between from about 10 degree to about 20 degree.

Using the dimensions described above (i.e., D1, D2, D3, H1, H2, H3, H4, α1, α2, and α3), the stent components of the stent-valves according to some embodiments of the present disclosure may be classified into different categories of sizes, such as small, medium, and large. Thus, according to a first group of embodiments, the stent components (or stent valves) may be sized as small, medium, and large according the following table.

TABLE 1

| | Small | Medium | Larger |
|---|---|---|---|
| Dl [mm] | 26-31 | 27-32 | 28-33 |
| D2 [mm] | 20-25 | 21-26 | 22-27 |

TABLE 1-continued

| | Small | Medium | Larger |
|---|---|---|---|
| D3 [mm] | 26-32 | 27-33 | 28-34 |
| HI [mm] | 4-8 | 4-8 | 4-8 |
| H2 [mm] | 7-11 | 8-12 | 9-13 |
| H3 [mm] | 11-15 | 13-17 | 15-19 |
| H4 [mm] | 14-22 | 15-23 | 16-24 |
| αl | 45°-65° | 45°-65° | 45°-65° |
| α2 | 15°-25° | 15°-25° | 15°-25° |
| α3 | 45°-90° | 45°-90° | 45°-90° |
| α4 | 5°-15° | 5°-15° | 5°-15° |

According to some embodiments, there is provided a replacement valve comprising a valve component and a stent component, wherein the stent component comprises a lower anchoring crown, an upper anchoring crown, a commissural post section, and stabilization arches. The conical body of the lower anchoring crown may slope outwardly from an inner diameter D2 to an outer diameter D3 in the direction of the proximal end, wherein the inner diameter D2 may be between about 20 mm to about 27 mm, especially between 20 mm to about 25 mm and wherein the outer diameter D3 may be between about 26 mm to about 33 mm, especially between 26 mm and 32 mm. The axial distance between the planes of the diameters D2 and D3 in the expanded configuration (H2) may be between about 7 to about 11 mm, wherein the outward slope of the lower anchoring crown is defined by an angle α2, which may be between from about 15 degree to about 25 degree. The conical body of the upper anchoring crown may slope outwardly from an inner diameter D2 to an outer diameter D1 in the direction of the distal end, wherein the inner diameter D2 may be between about 20 mm to about 27 mm, especially between 20 mm and 25 mm, and wherein the outer diameter D1 may be between about 26 mm to about 33 mm, especially between 26 mm and 31 mm.

The axial distance between the planes of the diameters D2 and D1 in the expanded configuration (H1) may be between about 4 to about 8 mm. The outward slope of the lower anchoring crown may be defined by an angle α1, which may be between from about 45 degree to about 65 degree. The end of the upper anchoring crown may form a tip, wherein the tip is bent inwardly toward the longitudinal axis at an angle α3. The angle α3 may be between from about 45 degree to about 65 degree. The length of the combined upper anchoring crown and commissural posts of the stent component (H3) may be between about 11 to about 15 mm. The length of the stabilization arches of the stent component (H4) may be between about 14 to about 30 mm (preferably up to about 22 mm); wherein the stabilization arches of the stent component expands outwardly at an angle α4 from a longitudinal axis toward the second distal end of the replacement valve. The angle α4 may be between about 5 degree to about 15 degree.

According to some embodiments, there is provided a replacement valve comprising a valve component and a stent component, wherein the stent component comprises a lower anchoring crown, an upper anchoring crown, a commissural post section, and stabilization arches. The conical body of the lower anchoring crown may slope outwardly from an inner diameter D2 to an outer diameter D3 in the direction of the proximal end. The inner diameter D2 may be between about 21 mm to about 26 mm, and the outer diameter D3 may be between about 27 mm to about 33 mm. The axial distance between the planes of the diameters D2 and D3 in the expanded configuration (H2) may be between about 8 to about 12 mm. The outward slope of the lower anchoring crown may be defined by an angle α2, which may be between from about 15 degree to about 25 degree. The conical body of the upper anchoring crown may slope outwardly from an inner diameter D2 to an outer diameter D1 in the direction of the distal end. The inner diameter D2 may be between about 21 mm to about 26 mm, and the outer diameter D1 may be between about 27 mm to about 32 mm. The axial distance between the planes of the diameters D2 and D1 in the expanded configuration (H1) may be between about 4 to about 8 mm. The outward slope of the lower anchoring crown is defined by an angle α1, which may be between from about 45 degree to about 65 degree. In some embodiments, the end of the upper anchoring crown forms a tip, wherein the tip is bent inwardly toward the longitudinal axis at an angle α3, which may be between from about 45 degree to about 65 degree. The length of the combined upper anchoring crown and commissural posts section of the stent component (H3) may be between about 13 to about 17 mm. The length of the stabilization arches and of the stent component (H4) may be between about 15 to about 23 mm. In some embodiments, the stabilization arches of the stent component expand outwardly at an angle α4 from a longitudinal axis toward the second distal end of the replacement valve. The angle α4 is between about 5 degree to about 15 degree. According to some embodiments, there is provided a replacement valve comprising a valve component and a stent component, wherein the stent component comprises a lower anchoring crown, an upper anchoring crown, a commissural post section, and stabilization arches. The conical body of the lower anchoring crown may slope outwardly from an inner diameter D2 to an outer diameter D3 in the direction of the proximal end. The inner diameter D2 may be between about 22 mm to about 27 mm, the outer diameter D3 may be between about 28 mm to about 34 mm, and the axial distance between the planes of the diameters D2 and D3 in the expanded configuration (H2) may be between about 9 to about 13 mm. The outward slope of the lower anchoring crown may be defined by an angle α2, and wherein α2 is between from about 15 degree to about 25 degree. The conical body of the upper anchoring crown slopes outwardly from an inner diameter D2 to an outer diameter D1 in the direction of the distal end, wherein the inner diameter D2 may be between about 22 mm to about 27 mm, and wherein the outer diameter D1 may be between about 28 mm to about 33 mm. The axial distance between the planes of the diameters D2 and D1 in the expanded configuration (H1) may be between about 4 to about 8 mm; wherein the outward slope of the lower anchoring crown is defined by an angle α1, which may be between from about 45 degree to about 65 degree. The end of the upper anchoring crown may form a tip, wherein the tip is bent inwardly toward the longitudinal axis at an angle α3, which may be between from about 45 degree to about 65 degree. The length of the combined upper anchoring crown and commissural post section of the stent component (H3) may be between about 15 to about 19 mm. The length of the stabilization arches and of the stent component (H4) may be between about 16 to about 24 mm. The stabilization arches of the stent component expands outwardly at an angle α4 from a longitudinal axis toward the second distal end of the replacement valve, wherein α4 is between about 5 degree to about 15 degree.

In some embodiments, multiple fixation elements (e.g., 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, etc. or 2 to 5, 2 to 10, 2 to 20, 2 to 30, 2 to 40, etc.) may be provided for holding the stent onto a catheter whereas a matching/complimentary element (e.g., stent holder with pins) may be attached to the delivery device. The design of the multiple fixation elements (e.g., forming "holes") may allow for the fixation of the stent onto the catheter only when the stent is crimped. The fixation may release automatically when the stent starts to expand. That is, the shape of the stent in the unexpanded state is designed to have holes or free areas that can be used to couple the stent with a stent holder. When the stent is expanded, the expanded configuration is absent such holes or free spaces and thus the stent automatically becomes uncoupled or releases from the stent holder upon expansion.

Figure 2E:
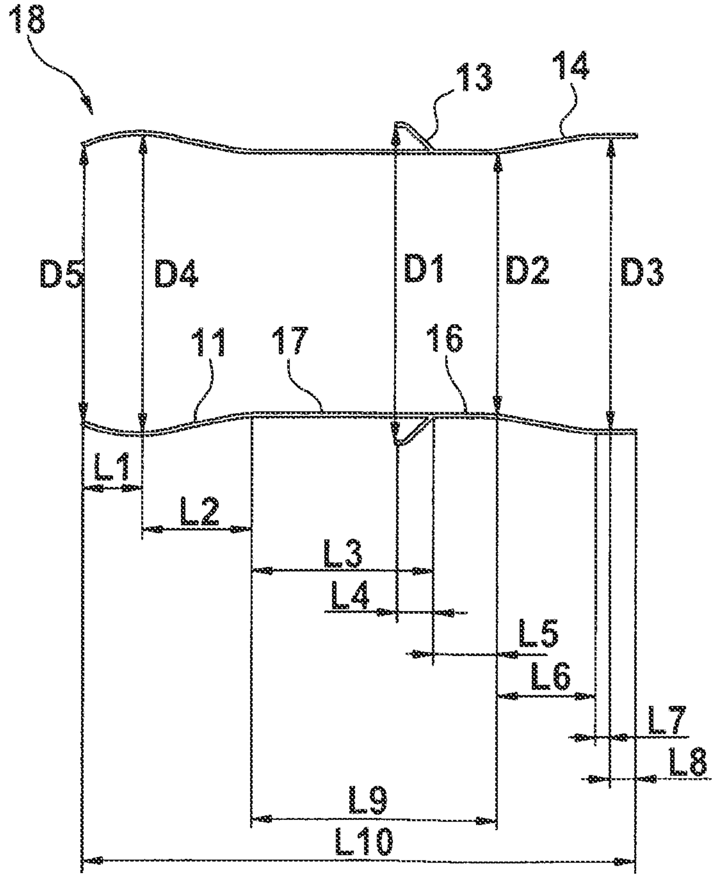
Figure 10:
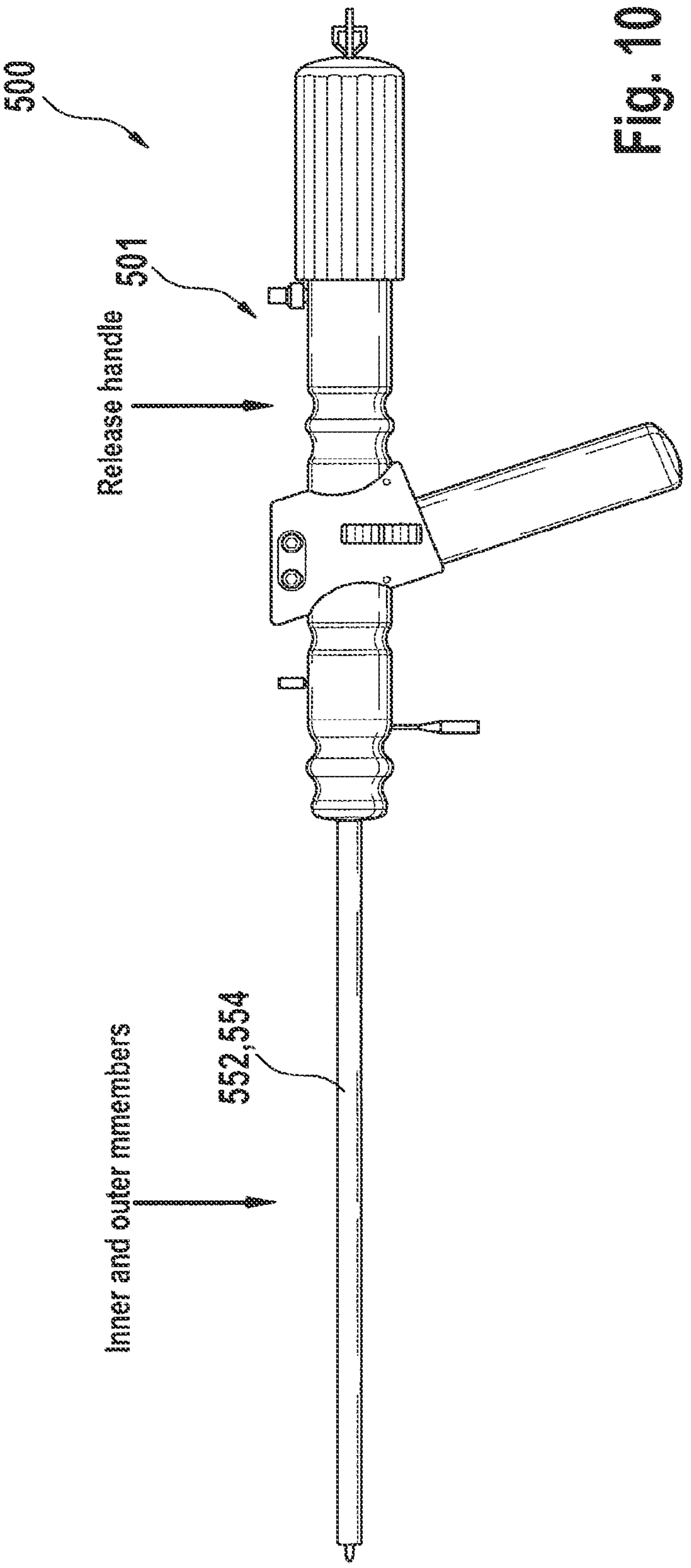
Figure 12:
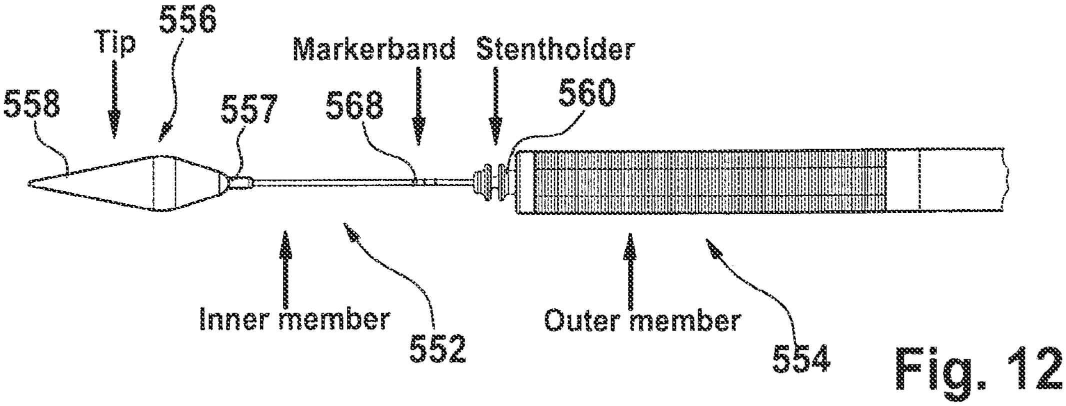

The stent component may further include at least one or a plurality (e.g., 2, 3, 4, 5, 6, 7, 8, 9, 10, etc.) of attachment elements at the proximal end of the stent, wherein the attachments elements are capable of mating with a stent holder 560 of a delivery device 500 (see FIGS. 10 and 12). The attachment elements may include a crochet-like configuration that engages, for example, a groove or other opening within the stent holder 560. Such attachment elements may be formed in the shape of a bent, or curved angled member (e.g., an "L" or "J" like shape). See FIG. 2D. In some embodiments, such attachment elements may be a hook (e.g., a "J" like shape). In the embodiment illustrated in FIG. 2D, the attachment element may be provided in an angled shape, for example, that extends from the body of the stent inwardly toward a central, longitudinal axis of the stent. The opening in the stent holder 560 (e.g., groove) may allow for a safe release of the stent upon rotation of the delivery system (e.g., a portion, all or members thereof—e.g., rotation of the stent holder). For example, when rotating the delivery system/stent holder, the end of the attachment element slides onto a surface (e.g. a ramp extending in the circumferential direction) and is thereby forced, according to some embodiments, to disengage the stent holder when reaching an edge (e.g. radially outermost end of ramp). As shown in FIG. 2E in some embodiments there is a cylindrical section 16 between the upper conical crown 13 and the lower conical crown 14. The cylindrical section 16 may further extend to form commissural posts, such that the axial profile shows a further cylindrical section 17 between the upper conical crown 13 and the stabilisation arches 11.

The distal part 18 of the stabilisation arches 11 is inclined inwardly, such that the arms of the stabilisation arches 11 are bulged to allow the distal stent section adapting at the inside of the aorta.

Using the dimensions as referenced in FIG. 2E, the stent components of the stent-valves according to alternative preferred embodiments of the present disclosure may be classified into different categories of sizes, such as small, medium, and large. Thus, according to some embodiments, the stent components (or stent valves) may be sized as small, medium, and large according the following table.

TABLE 2

| | Small | Medium | Large |
|---|---|---|---|
| D1 [mm] | 26.5-28.5 | 28.8-30.8 | 30.9-32.9 |
| D2 [mm] | 21.6-23.6 | 23.6-26.6 | 25.6-27.6 |
| D3 [mm] | 24.8-26.8 | 27-29 | 29.1-31.1 |
| D4 [mm] | 26-28 | 28-30 | 30-32 |
| D5 [mm] | 24.1-26.1 | 26.4-28.4 | 28.5-30.5 |
| L1 [mm] | 3.5-4.9 | 3.5-4.9 | 3.5-4.9 |
| L2 [mm] | 10.0-11.2 | 9.9-11.1 | 9.7-10.9 |

TABLE 2-continued

| | Small | Medium | Large |
|---|---|---|---|
| L3 [mm] | 13.9-14.9 | 15.1-16.1 | 16.1-17.1 |
| L4[mm] | 3.0-4.0 | 3.0-4.0 | 3.0-4.0 |
| L5 [mm] | 4.5-5.5 | 4.5-5.5 | 4.5-5.5 |
| L6 [mm] | 7.1-8.1 | 7.5-8.5 | 7.7-8.8 |
| L7 [mm] | 1.0-2.0 | 1.0-2.0 | 1.0-2.0 |
| L8 [mm] | 1.9-2.9 | 1.9-2.9 | 1.9-2.9 |
| L9 [mm] | L3 + L4 | L3 + L4 | L3 + L4 |

D1 represents the diameter of the stent component at the distal edge of the outwardly sloping upper conical crown in the expanded configuration.

D3 represents the diameter of the most proximal edge of the stent component in the expanded configuration D2 represents the diameter of the stent component at the cylindrical section between the upper and lower anchoring crowns in the expanded configuration.

D4 represents the diameter of the stent component at the junction between the outwardly and inwardly bent sections of the stabilization arches in the expanded configuration, D5 represents the diameter of the stent component at the most distal edge of the stent in the expanded configuration.

L1 represents the axial length of the inwardly bent part of the stabilization arches.

L2 represents the axial length of the outwardly sloping part of the stabilization arches.

L3 represents the axial length of the cylindrical section between the upper anchoring crown and the stabilization arches.

L4 represents the axial length of the conical part of the upper anchoring crown in the expanded configuration.

L5 represents the axial length of the trunk section between conical part of the upper anchoring crown and the conical part of the lower anchoring crown.

L6 represents the axial length of the outwardly sloping conical part of the lower anchoring crown in the expanded configuration.

L7 represents the axial length of the proximal cylindrical part of the lower conical crown.

L8 represents the axial length of the axial extensions forming attachment elements.

L9 represents the axial length of the cylindrical section between the stabilization arches and the lower conical crown.

Figure 2F:
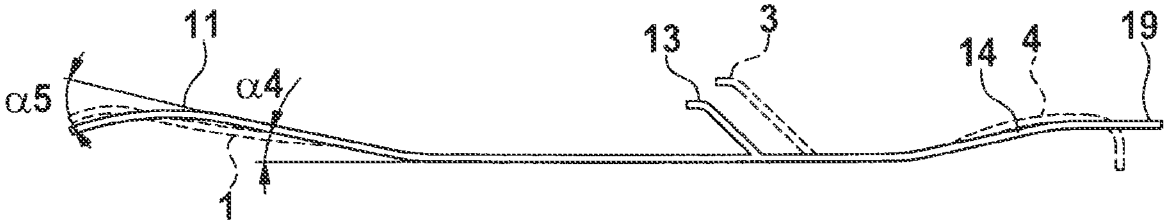

The total length L10 of the stent thus results in a range of 41 mm to 49 mm. As compared with Table 1, the dimensions have been further improved as explained below, for example the diameter D1 has been reduced by about 2 to 3 mm. FIG. 2F shows in comparison a first embodiment according to Table 1 (in dashed lines) and a second preferred embodiment according to Table 2 in plain lines.

When the final position of the stent is determined by a friction fit between the upper crown and the leaflets of the native valve it can be seen that a stent according to the second preferred embodiment may sit lower within the native valve as compared to the first embodiment and thus the commissural posts including the valve of the second preferred embodiment rests closer to the native annulus.

It has been observed in vivo that some embodiments of the stent component may allow for self-positioning of the replacement valve under diastolic pressure. Once delivered slightly above the aortic annulus, the stent-valve migrates toward the left ventricle due to the forces caused by the diastolic pressure until it reaches a stable position given by the shape/radial force of the anchoring crowns, the compliance of the aortic annulus, and presence of any calcification.

In some other embodiments, the presence of calcification deposits at the native valve may limit or prevent sliding movement of the valve from a release position to a different stable position. In that case, the stable position may be the same as the release position.

In some embodiments, a stent-valve suitable for implanting at a calcified native valve site comprises an upper (first) crown section comprising at least a portion diverging outwardly in a direction towards an aortic end of the stent-valve. The upper crown section may have a free end (e.g. proximal of the distal end of the stent component). The upper crown/divergent portion may have an angle of divergence (or inclination or conical angle) with respect to the stent axis of less than 60 degrees (preferably 50 degrees or less, preferably 45 degrees or less, for example 43-45 degrees) and/or have an axial length of less than 10 mm (preferably less than 8 mm, preferably less than 6 mm, preferably less than mm, for example, 3-4 mm). Such dimensions (see e.g. the embodiment in FIG. 2H shown in continuous line as compared to the embodiment in dashed lines) may be regarded as less sculpted than in some other designs. The dimensions can nevertheless provide a reliable abutment surface to resist migration of the stent-valve towards the ventricle during ventricular diastole, without the upper crown being so large and/or having an aggressive angle of inclination that the positioning is likely to be affected adversely by the calcified deposits.

Additionally or alternatively, a stent-valve suitable for implanting at a calcified valve site comprises an upper (first) crown comprising at least a portion diverging outwardly in a direction towards an aortic end of the stent-valve. A substantially non-diverging region 16 (see e.g. FIG. 2E) communicating with the narrow end of the diverging portion may extend therefrom in a direction towards the ventricular end of the stent-valve. The term "substantially non-diverging" may mean a divergence of no more than 10 degrees, preferably less than 8 degrees, preferably less than 6 degrees, preferably less than 5 degrees, preferably less than 4 degrees, and preferably zero degrees. The substantially non-diverging region may have an axial length L5 (see FIG. 2E) of at least 1 mm, preferably at least 2 mm, preferably at least 3 mm, preferably at least 4 mm, for example, 4.5-5.5 mm. Provision of such a substantially non-diverging region may enable the stent-valve to better accommodate calcified deposits where the stent-valve passes through the native valve and/or native annulus. The substantially non-diverging region may separate (at least a portion of) the upper (first) crown from (at least a portion of) the lower (second) crown. The substantially non-diverging section may form a part of the upper crown section and/or lower crown section.

Additionally or alternatively, a stent-valve suitable for implanting at a calcified valve site comprises a lower crown section. The lower crown section may comprise at least a portion diverging outwardly in a direction towards the ventricular end of the stent valve. The lower crown and/or divergent portion may be provided at a portion of the stent-valve intended to be received at the ventricle, for engaging native tissue to resist migration of the stent-valve in a direction out of the ventricle. The divergent portion of the lower crown section may have an angle of divergence with respect to the stent-valve axis of between 10 degrees and 20 degrees (preferably 10-16 degrees, more preferably 10-15 degrees, more preferably 10-14 degrees, more preferably 10-13 degrees). Such an angle of divergence may be regarded as less sculpted than some other designs (see e.g. the embodiment in FIG. 2H shown in continuous line as compared to the embodiment in dashed lines). However, the angle permits the lower crown to function to resist migration, while being versatile in accommodating a wide range of calcifications without affecting function.

In one proposal, an upper crown of a stent-valve is provided that is not too large (see e.g. the embodiment in FIG. 2H shown in continuous line as compared to the embodiment in dashed lines having a larger crown), the axial length L4 being between 3 and 4 mm and the angle 1 of the upper crown being between 43° and 45°, as well as the length of the cylindrical part 16 being not too small, the length L5 being between 4.5-5.5 mm. Stents of this type do not block the coronary arteries or contact the sinus of the Vasalva, they reduce the risk of coronary occlusion and they even fit to a calcified annulus.

In a preferred embodiment the lower crown comprises a relatively small conical angle of about 10° to about 13° and a cylindrical proximal section with an axial length of about 1-2 mm. Stents of this type allow a homogeneous seating towards a calcified annulus and less turbulences within the valve inflow.

In a further preferred embodiment the stent stabilization arches 11 are bent inwardly with a relatively big radius of the curvature to avoid injuries of the ascending aorta.

FIG. 2F shows a comparison of different embodiments in a side view. The side view pictured in dashed lines represents a first embodiment corresponding to Table 1 and FIGS. 2A-2D. The side view shown in a continuous line represents a second preferred embodiment corresponding to Table 2 and FIG. 2E.

As can be seen in FIG. 2F in the preferred embodiments the outwardly sloping angles of the upper conical crown 13 and lower conical crown 14 have been reduced, whereas the outwardly sloping angle of the stabilization arches 11 is slightly larger in the preferred embodiments. The total length of the upper conical crown 13 has been shortened by shortening the axially extending tip. The distance between the upper and lower conical crown in the preferred embodiments according to Table 2 is longer than in the first embodiments according to Table 1.

In the example shown in FIG. 2F the lower anchoring crown 14 may have axial extensions 19 each forming a respective attachment element. Preferably the attachment element comprises an opening for receiving a pin arranged on the stent holder of the delivery system.

Figure 2G:
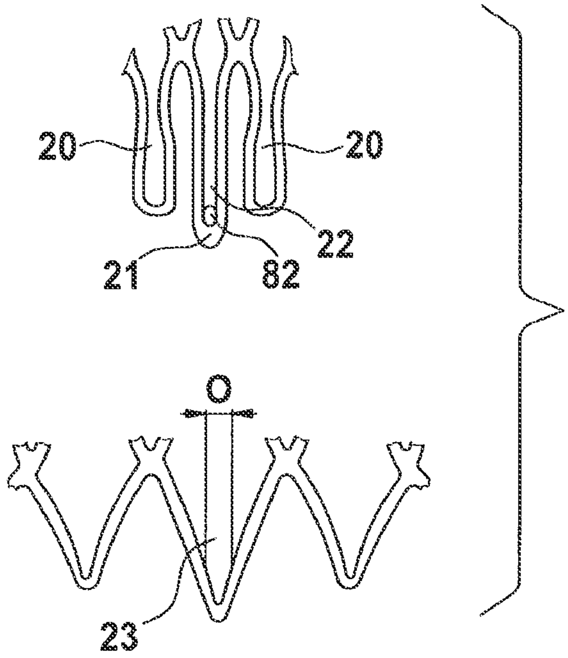
Figure 2H:
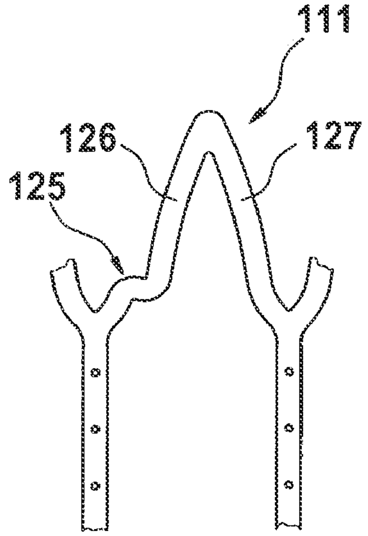
Figure 2L:
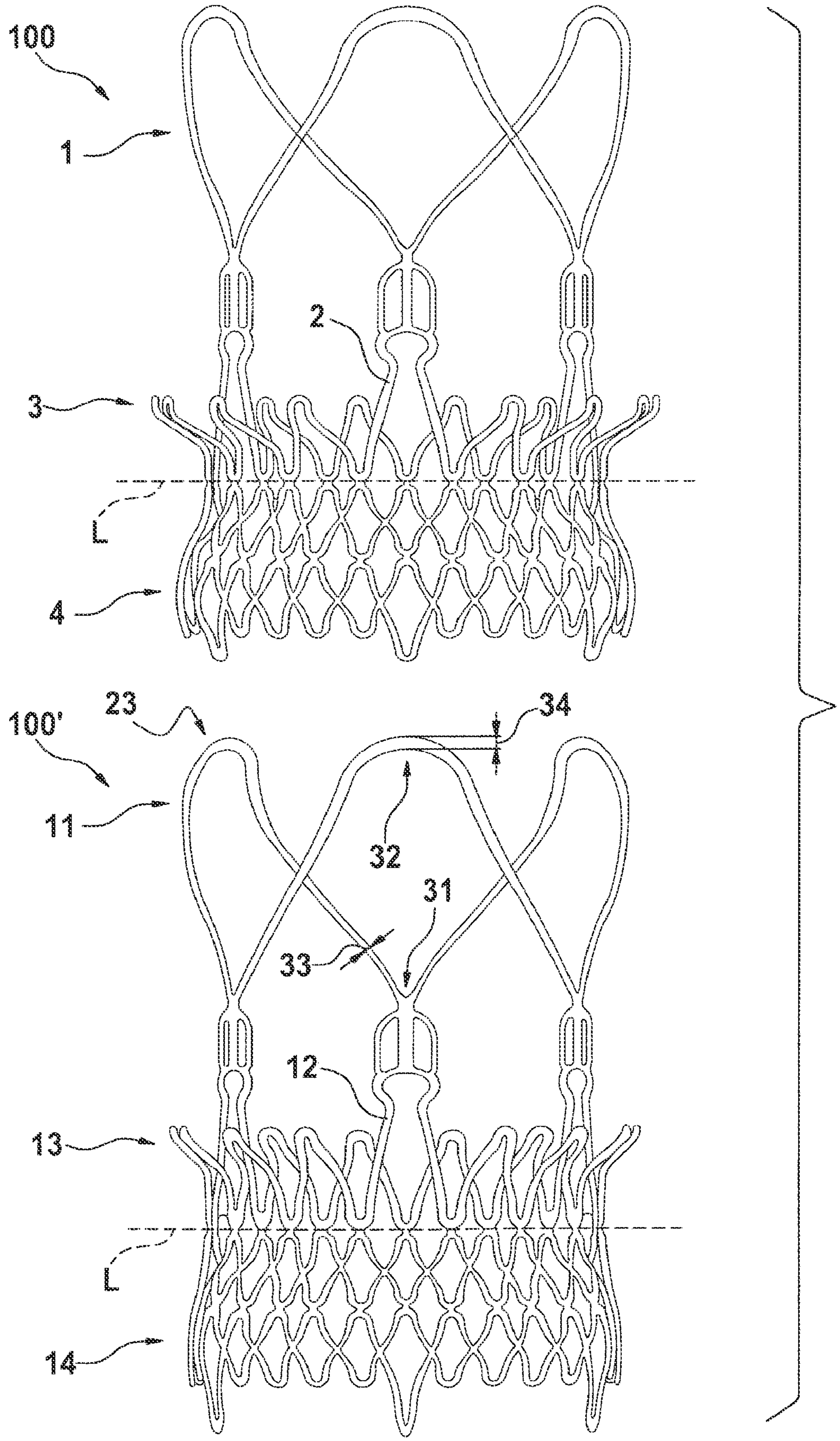

Preferably the lower anchoring crown comprises cells 20 and the extension is formed by an elongation 21 of at least one cell 22 as shown in FIG. 2G.

The upper part of FIG. 2G shows a side view of cells of the lower anchoring crown in a non-expanded configuration. The elongation 21 of the cell 22 defines an opening 23 for engagement with a pin 82. When the sheath has been removed from the stent and the stent radially expands, the aperture size (e.g., diameter O) of the opening 23 enlarges as shown in the lower part of FIG. 2G.

The elongation 21 may be received by an axial groove arranged on the stent holder of the delivery system.

FIG. 2H shows a side view of a stabilization arch 111 of a specific embodiment. In this embodiment one arm 126 of the arch 111 comprises a pattern 125, in this case two kinks, such that the arm 126 is different from the other arm 127 of the arch 111 and may be distinguished from the other arm 127 in a projected image, such as an x-ray image.

In some embodiments, a valved-stent delivery system, and method for delivering the valved-stent to an implantation site are provided in which the valved-sent is expanded at the implantation site in a stepwise manner (for example) from its distal end towards its proximal end. For example, a release procedure for causing expansion of a valved-stent may involve pulling back a sheath element on a catheter delivery device. The sheath element, in such an embodiment, constrains the valved-stent toward a section of the heart (for example, the left ventricle of the heart). According to such a procedure, there may be no interaction of the delivery system with the anatomy of the ascending aorta/aortic arch. For example, the sheath constraining the valved-stent, and the tip of the delivery system may not be required to enter the aortic arch during the release procedure, which is beneficial since such entry potentially can cause a bending moment acting onto the valved-stent and result in inaccurate positioning of the valved-stent (e.g., tilting). According to some embodiments, there is provided a replacement heart valve comprising: a valve component; and a stent component to which the valve component is affixed thereto, the stent component comprising a longitudinal axis; a lower anchoring crown including a substantially conical shape having a narrow end, a broad end and a predetermined first height; and an upper anchoring crown including a substantially conical shape having a narrow end, a broad end and a predetermined second height, wherein: a center of each of the lower anchoring crown and upper anchoring crown are arranged to align substantially with the longitudinal axis; the narrow ends of the lower and upper anchoring crowns are arranged to meet forming an annular groove to receive the annulus of a failed heart valve at an implantation site of the heart, and the first height of the lower anchoring crown is greater than the second height of the upper anchoring crown.

FIG. 21 illustrates two examples of aortic bioprosthesis or stented replacement valves 100 and 100' according to some embodiments.

According to these embodiments the upper anchoring crown 3, 13 and the lower anchoring crown 4, 14 meet at a line L, from where the commissural posts 2, 12 extend.

The curvature 31 between two adjacent stabilization arches 11 corresponds to a radius which is much smaller than the curvature 32 at the tip of the stabilization arches 11. Thus the arches 11 extend more upwardly than outwardly from the commissural posts 12 and the risk of contacting tissue in this region is reduced.

Additionally the thickness 33 of material of the stabilization arch at its base near the section where it communicates with the commissural posts 12 is smaller than the material thickness 34 at the tip 23. Thus the surfaces of the stabilization arches 11 which face against the inner wall of the aorta are relatively wide such that the risk of cutting arterial tissue is reduced, whereby the stabilization arches 11 at there base are not too rigid.

The tips 23 of the stabilization arches 11 turn at least partly towards the central axis of the stent. The stabilization arch 11 in its entire lengths may be divergent but with reduced divergence at the tip 23 portion. Thus the stabilization arches 11 have a shovel-shape like envelope, which on the one hand supports positioning of the stent and the other hand reduces the risk of injuring the surrounding tissue.

Cardiac Stem Valve Delivery System

The present invention further provides for a delivery system for delivering the stent-valves of the present invention. Some embodiments of the present disclosure provide a cardiac stent-valve delivery system that includes an inner assembly and an outer assembly. The inner assembly may include a guide wire lumen (e.g., polymeric tubing) and a stent holder for removable attachment to a stent-valve. The outer assembly may include a sheath. The inner member and the outer member may be co-axially positioned and slidable relative to one another in order to transition from a closed position to an open position, such that in the closed position the sheath encompasses the stent-valve still attached to the stent holder and thus constrains expansion of the stent-valve. In the open position, the outer sheath may not constrain expansion of the stent-valve and thus the stent-valve may detach from the stent holder and expand to a fully expanded configuration.

FIGS. 10-14 illustrate the delivery device 500 according to some embodiments. The delivery system allows for a minimally-invasive surgical approach whereby valve replacement surgery is performed on a beating heart without the need for an open-chest cavity and heart-lung bypass. In some embodiments, the heart is penetrated trans-apically through a relatively small opening in the patient's chest (e.g., an intercostal space—a region between two ribs). From this access point, the left ventricle is penetrated at the apex of the heart.

The delivery device 500 is used to position and release the aortic bioprosthesis or stented replacement valve 100 at the intended location over the patient's native, calcified aortic valve via transapical access. In some embodiments, the delivery system comprises the following components: a flexible inner member 552; flexible outer member 554; and a release handle 501.

In some embodiments, the flexible inner member 552 contains a guide wire lumen bonded proximally to a female luer lock and distally to a radio-opaque atraumatic tip 556. In some embodiments, the flexible inner member 552 may further comprise a stent holder, which may be added to avoid premature delivery of the aortic bioprosthesis during the release procedure. In some embodiments, the flexible inner member 552 may further comprise a radio-opaque marker-band for the accurate positioning of the implant. The inner member is fixed proximally to the release handle In some embodiments, the flexible outer member 554 contains distally the compressed aortic bioprosthesis and is fixed proximally to the trigger of the release handle. Both flexible members may be coaxially arranged and longitudinally slideable.

In some embodiments, the delivery device 500 comprises a release handle 501, which provides an ergonomic fit to the physician's hand to facilitate the deployment of the aortic bioprosthesis 100. In some embodiments, the delivery device 500 may comprise one or more of the following features (see FIG. 11): Check valve 520 for flushing of the annular space between the inner and outer member; Safety button 510 to avoid premature release of the implant; Release button 505 to allow partial/full release of the implant; and Trigger 520 for releasing the aortic bioprosthesis from the delivery system.

In some embodiments, the delivery system has a crossing profile of 33F, a usable length of min. 330 mm, and is compatible with 0.035" guide wires. The delivery system accepts all the different sizes of the aortic bioprosthesis or stented replacement valve 100.

The device preparation before use may comprise one or more of the following optional preparation steps: Rinsing the stent-valve 100 in 4 different baths containing 500 ml of sterile saline solution during a minimum of 3 min in each bath (min. total 12 min rinsing duration) to remove residuals of the sterilant solution; Crimping the stent-valve 100 onto the Transapical Delivery System by means of a crimper (e.g., MSI crimper HV200-104-40); and Flushing of the delivery system.

Figure 13:
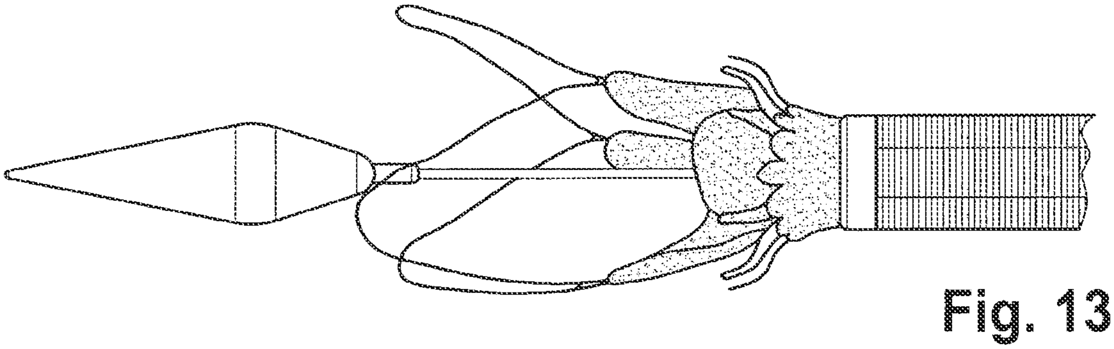
Figure 14:
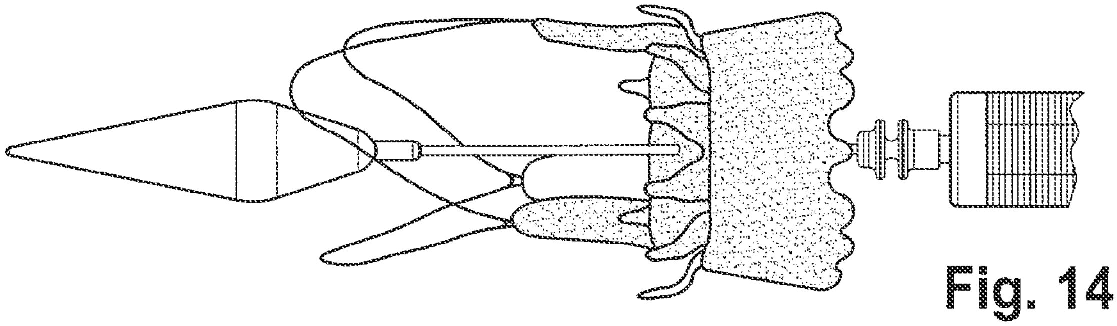
Figure 15:
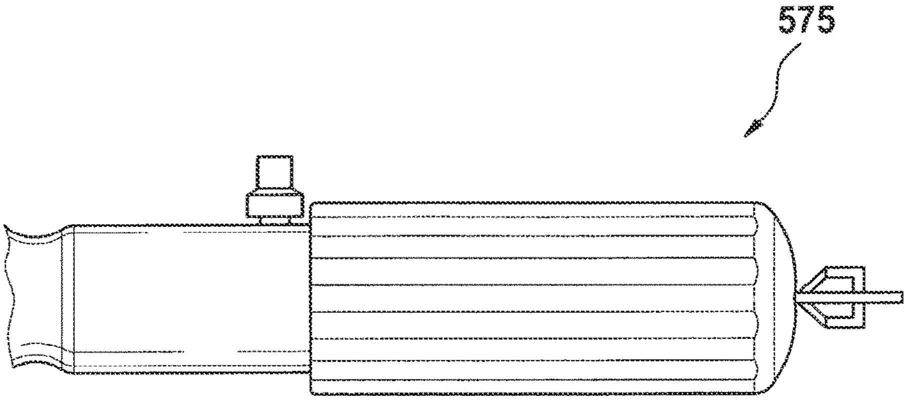

At this stage, the delivery system might be inserted over the wire into the left ventricle. An introducer sheath may optionally be used through which the delivery device is inserted. However, in the illustrated example, the outer member 554 (FIG. 12) of the delivery device may have a generally uniform diameter along at least the portion of its length intended to be inserted. Such a uniform diameter may enable the delivery device to be inserted into the left ventricle without the need for an additional introducer sheath. Avoiding an introducer sheath may enable a smaller puncture aperture in the ventricle wall, because the puncture does not need to accommodate a wall thickness of an introducer sheath in addition to the delivery device. The following exemplary steps may be performed in order to release the stent-valve 100: Unscrewing and removal of the safety button; Fluoroscopic positioning of the crimped stent-valve 100 at the intended location by mean of the radioopaque markerband located onto the inner member (e.g., at the level of the groove D2); Partial delivery of the stent-valve 100 under fluoroscopic control by pulling back the trigger with the release button 505 in "partial release" position (FIG. 13). At this stage, the stabilization arches are fully deployed and the upper anchoring crown partially or fully deployed. Pulling back of the trigger 520 causes a backward movement of the outer member relative to the inner member and thus a partial delivery of the implant; Final delivery of the partially deployed stent-valve 100 under fluoroscopic control upon appropriate positioning by pulling back the trigger with the release button in "full release" position (FIG. 14).

When deployed, the stent-valve 100 automatically detaches from the stent holder due to the self-expandable properties of the stent thereby leaving the upper and lower crown fully expanding over the native leaflets respectively within the left ventricle outflow tract. Careful withdrawal of the delivery system tip 556 through the fully deployed and functional bioprosthesis under fluoroscopic control to avoid any valve dislodgement. The delivery system may be closed by pushing forward the trigger and withdrawal of the delivery system through the sheath introducer.

Figure 11:
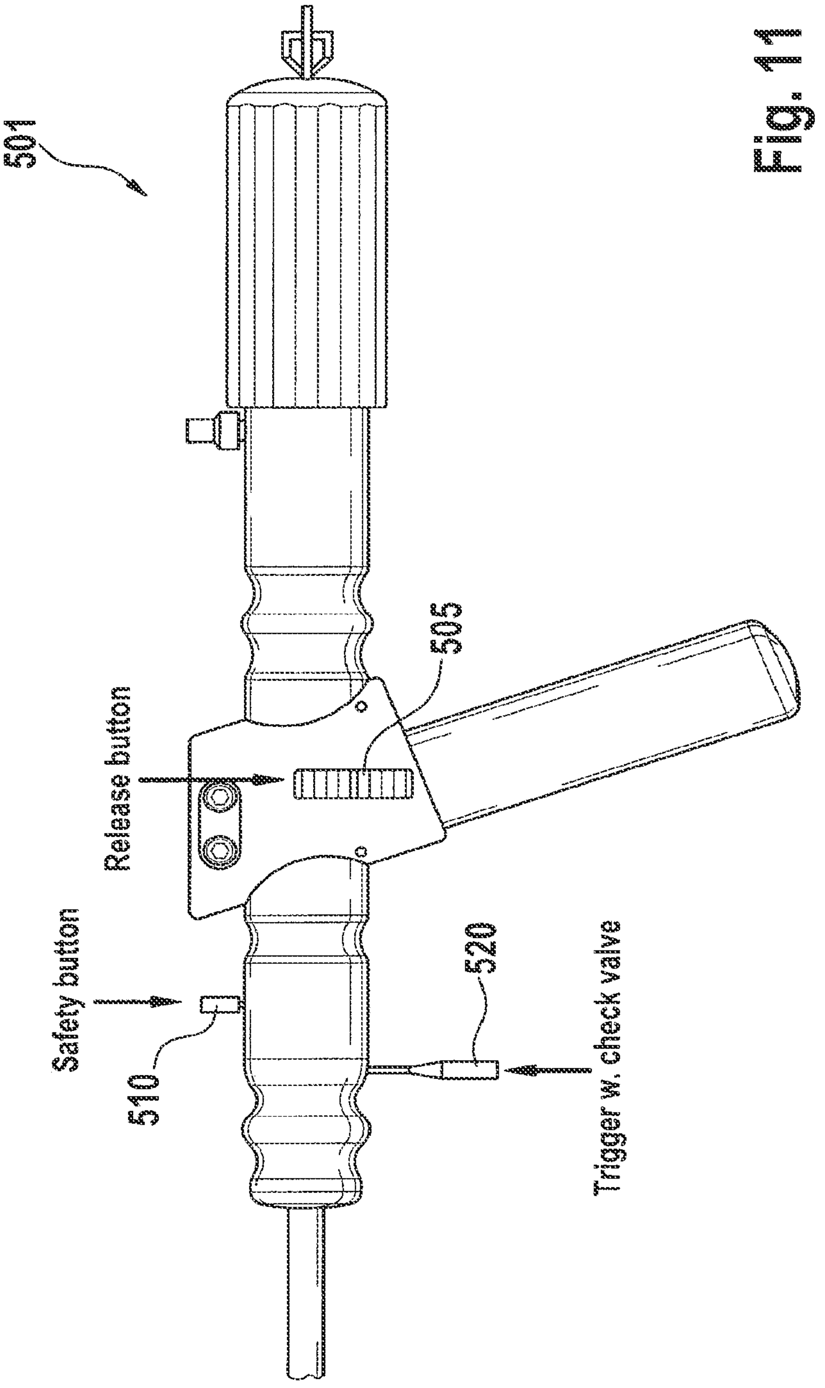

FIG. 10-12 shows a delivery system 500 for distal-to-proximal expansion of a stent-valve 100, according to some embodiments of the present disclosure. In some embodiments of the delivery system, the system 500 may include an inner member 552 and an outer member 554 (e.g., sheath) which are co-axially positioned and slidable one against the other. The inner member 552 may comprise tubing (e.g., polymeric tubing) which serves as a guide wire lumen and on which at least one of (and preferably several or all) a tip 556, a fluoroscopic marker 568 (e.g., radioopaque marker band), and a stent-holder 560 are affixed (e.g., bonded). The polymeric tubing may be reinforced proximally with a rigid (e.g., stainless steel) shaft. A luer connector may be affixed to a stainless steel shaft to allow flushing of the guide wire lumen with saline (for example). The outer member 554 may comprise a distally arranged sheath which may be used to constrain the stent in a closed/contracted (e.g., substantially non-expanded) configuration. Proximally, the sheath may be fixed to a hemostasis valve to allow the flushing of the annular space between the inner and outer members with saline (for example). As illustrated, the diameter of the outer member 505 may be substantially uniform at least along a portion of its length intended to be inserted through the ventricle wall. In some other embodiments, the diameter of the outer member may vary over its longitudinal direction (e.g., smaller diameter proximally to decrease the bending stiffness of the delivery system). As explained above, the deployment of the stent-valve may be controlled by pulling back a trigger of or at the delivery device handle. In some other embodiments, the deployment of the stent-valve may occur by holding the inner member at the level of the stainless steel shaft with one hand and the outer member at the level of the hemostasis valve with the other hand. Then, upon positioning of the replacement valve (e.g., under fluoroscopic control), the outer member is pulled back with the inner member being kept at its original position, until the stent is fully deployed.

In some embodiments, at any time during the deployment procedure, until the configuration described in FIG. 13 (e.g., immediately before the final release of the device from the valve holder), the movement of the outer member 554 (i.e. the valve sheath) may be reversed, allowing the "recapture" of the device inside the delivery system. The recapturing mechanism of the delivery device may be activated by turning the recapture control knob 575, which may be placed at the proximal end of the delivery system. The bioprosthesis 100 is held in place by inflow hooks (see hooks 5 in FIG. 2A) and/or one or more attachment elements of the bioprosthesis engaging the stent holder 560, while the knob 575, advancing on a thread, slides back the valve sheath to re-close the prosthesis. This feature allows either the repositioning or the entire retrieval of the prosthesis from the implant side at any time of the procedure before the final release.

In some embodiments, the tip of the delivery system may be in two parts, which can be easily disconnected. The inner part 557 may optionally be of metallic material, while the conical distal part 558 may optionally be of a polymeric material. The conical distal part 558 forms the actual tip of the delivery system. With this arrangement, the large tip of the delivery system can be removed whenever it is needed or desired, e.g., during crimping of the stent-valve 100 and/or loading of the crimped stent-valve 100 onto the delivery device.

Figure 16:
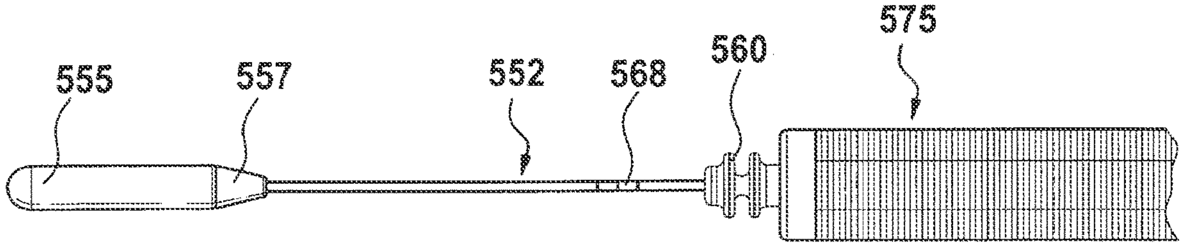

In some embodiments, a delivery system is provided with a temporary low-profile tip 555 (See FIG. 16). This configuration of the shaft of the delivery system allows the prosthesis 100 to cross easily over the tip during the crimping and/or mounting procedure mentioned above. Once the prosthesis is mounted, the tip may be rapidly exchanged with a conical tip 558, which may be used for the delivery process. During the mounting procedure, the low-profile tip 555 allows the introduction of the shaft thru the prosthesis 100, even when the prosthesis 100 is in a partially collapsed form. Advantages of crossing the valve over the tip when the prosthesis 100 is already partially collapsed includes, but is not limited to: better control and direct view of the arrangement of the prosthetic cusps during crimping (since the valve orifice is not occluded by any component), avoiding folds or entrapment of the tissue inside the frames of the stent. Finally, introduction of the smooth low-profile tip further promotes the proper leveling of the cusps, and may cancel the effect of the remaining part of the crimping.

In some embodiments, the inner assembly of the delivery device may include a fluoroscopic marker fixed to the guide wire lumen distal of the stent holder. In some embodiments, the diameter of the outer assembly of the delivery device varies over its longitudinal axis. In still other embodiments, the delivery system comprises a rigid (e.g., stainless steel) shaft in communication with a proximal end of the guide wire lumen. In some embodiments, the delivery system comprises a luer connector in communication with the rigid shaft.

In some embodiments, there is provided a cardiac stent-valve delivery system comprising: an inner assembly comprising a guide wire lumen and a stent holder for removable attachment to a stent-valve, wherein the stent-valve comprises at least one attachment element for removable attachment to the stent holder, wherein the at least one attachment element is located at a proximal end of the stent-valve, wherein the proximal end is defined as the end toward the left ventricle when delivered from a transapical approach; and an outer assembly comprising a sheath; wherein the inner member and the outer member are co-axially positioned and slidable relative to one another in order to transition from a closed position to an open position, such that in the closed position the sheath encompasses the stent-valve still attached to the stent holder constraining expansion of the stent-valve, and such that in the open position the outer sheath does not constrain expansion of the stent-valve allowing the stent-valve to detach from the stent holder and expand to an expanded configuration.

In some embodiments, the guide wire lumen comprises polymeric tubing. In some embodiments, the stent-holder may be fixed (directly or indirectly) relative to the guide wire lumen. A fluoroscopic marker may be fixed to the guide wire lumen distal of the stent holder. In some embodiments, a rigid shaft may be in communication with a proximal end of the guide wire lumen. A luer connector may be in communication with the rigid shaft. In some embodiments, the diameter of the outer assembly varies over its longitudinal axis.

According to some embodiments, there is provided a method for replacing an aortic valve within a human body, the method comprising: covering a stent-valve according to the present invention with a sheath in order to maintain the stent-valve in a collapsed configuration; transapically inserting the stent-valve still in the collapsed configuration into the human body; partially expanding the stent-valve by sliding the sheath towards the left ventricle of the heart, wherein said sliding of the sheath towards the left ventricle causes expansion of a distal end of the stent-valve while the proximal end of the stent-valve remains constrained by the sheath; and further sliding the sheath towards the left ventricle of the heart in order to substantially release the entire stent-valve such that the stent-valve is allowed to expand to an expanded configuration. The method may further comprise sliding the sheath in the opposite direction prior to said full expansion in order to recapture the stent-valve within the sheath.

According to some embodiments, there is provided a method for cardiac valve replacement comprising: releasing a distal end of a stent-valve according to the present invention from a sheath, wherein the distal end comprises a radiopaque marker; rotating the stent-valve, if necessary, to orient the stent-valve appropriately with respect to the coronary arteries; releasing stabilization arches of the stent-valve from the sheath, in order to cause at least one of the stabilization arches to contact the aorta; releasing an upper anchoring crown 3 of the stent-valve from the sheath, in order to cause the lower anchoring crown to contact native valve leaflets; and releasing a lower anchoring crown 4 of the stent-valve from the sheath, in order to cause the lower anchoring crown 4 to contact an annulus/inflow tract, wherein the lower anchoring crown 4 comprises the proximal section of the stent-valve and said releasing of the lower anchoring crown 4 comprises fully releasing the stent-valve from the sheath.

In some embodiments, the method for cardiac valve replacement comprises: releasing a distal end of a valved-stent according to the present invention from a sheath, wherein the distal end comprises a radiopaque marker and a plurality of stabilization arches; optionally rotating the valved-stent, if necessary, to orient the stent-valve appropriately with respect to the coronary arteries; releasing the stabilization arches of the valved-stent from the sheath, in order to cause at least one of the stabilization arches to contact an area above a native valve; releasing an upper anchoring crown portion 3 of the valved-stent from the sheath, in order to cause the upper anchoring crown to contact the native valve leaflets; and releasing a lower anchoring crown 4 portion of the valved-stent from the sheath, in order to cause the lower anchoring crown 4 to contact an annulus/inflow tract of the native valve, wherein the lower anchoring crown 4 is the proximal section of the stent-valve and said releasing the lower anchoring crown 4 comprises fully releasing the stent-valve from the sheath if used, the step of rotating the valved-stent may be performed before the step of releasing the distal end of the valved-stent, or after the step of releasing the distal end of the valved-stent.

In some embodiments, the method for cardiac valve replacement comprises: releasing a distal end of a valved-stent according to the present invention from a sheath before the proximal end is released. The distal end of the stent may not be the first part of the stent which is released from the sheath. An intermediate part may be released first from a sheath.

According to some embodiments, there is provided a replacement valve for use within a human body comprising: the replacement valve of the present embodiments comprising a valve component, a stent component comprising a lower anchoring crown, and upper anchoring crown, a commissural post section, and stabilization arches; wherein the stent component comprises at least one attachment element configured for removable attachment to a groove of a stent holder 560 of a delivery device 500. The commissural post section may optionally be generally cylindrical in shape, or generally conical, or some other form.

According to some embodiments, there is provided a method of implanting a replacement valve according to the present invention into a heart of a mammal comprising: delivering a replacement valve to an implantation site of the heart of the mammal, wherein: the implantation site comprises a release location and a final location; and the release location is spaced apart from the final location in a blood upflow direction; and releasing the replacement valve at the release location, wherein: the replacement valve slides into the final location upon at least one beat of the heart subsequent to the replacement valve being released at the release location.

According to some embodiments, there is provided a method of implanting a replacement valve according to the present invention into a heart of a mammal comprising: delivering a replacement valve to an implantation site of the heart of the mammal, wherein: the implantation site comprises a release location and a final location; and the release location is spaced apart from the final location at a predetermined distance in a blood upflow direction; and releasing the replacement valve at the release location, wherein: the replacement valve slides into the final location, preferably upon at least one beat of the heart, subsequent to the replacement valve being released at the release location.

In some embodiments, the predetermined distance comprises a range of between about 3 mm and about 20 mm; between about 7 mm to about 11 mm; between about 8 mm to about 12 mm; between about 9 mm to about 13 mm.

According to some embodiments, there is provided a method of implanting a replacement valve according to the present invention into a heart of a mammal comprising: delivering a replacement valve to an implantation site of the heart of the mammal, wherein: the stent is released with the stent axis being substantially aligned with the catheter axis but not being aligned with the main axis of the ascending aorta; and the main direction of the catheter axis is different from the main direction of the axis of the ascending aorta; and releasing the replacement valve, wherein: the replacement valve moves into the final orientation thereby at least partly tilting such that the axis of the stent substantially aligns with or at least closer to the main axis of the ascending aorta or the root of the ascending aorta, subsequent to the replacement valve being released. The stabilization arches support the alignment.

Preferably the stent is released in a release location. Subsequent to the replacement valve being released at the release location the stent slides into its final location and/or tilts into its final orientation.

In some embodiments, one or more attachment elements 565 may serve to hold the stent-valve onto the delivery system until full release of the stent during delivery/implantation, thus allowing for, in some embodiments, the recapture of the stent upon partial release. The attachment elements 565 may also prevent the stent from "jumping out" of the delivery system just prior to its full release—such jumping out may result in inaccurate positioning of the implant.

Figure 17:
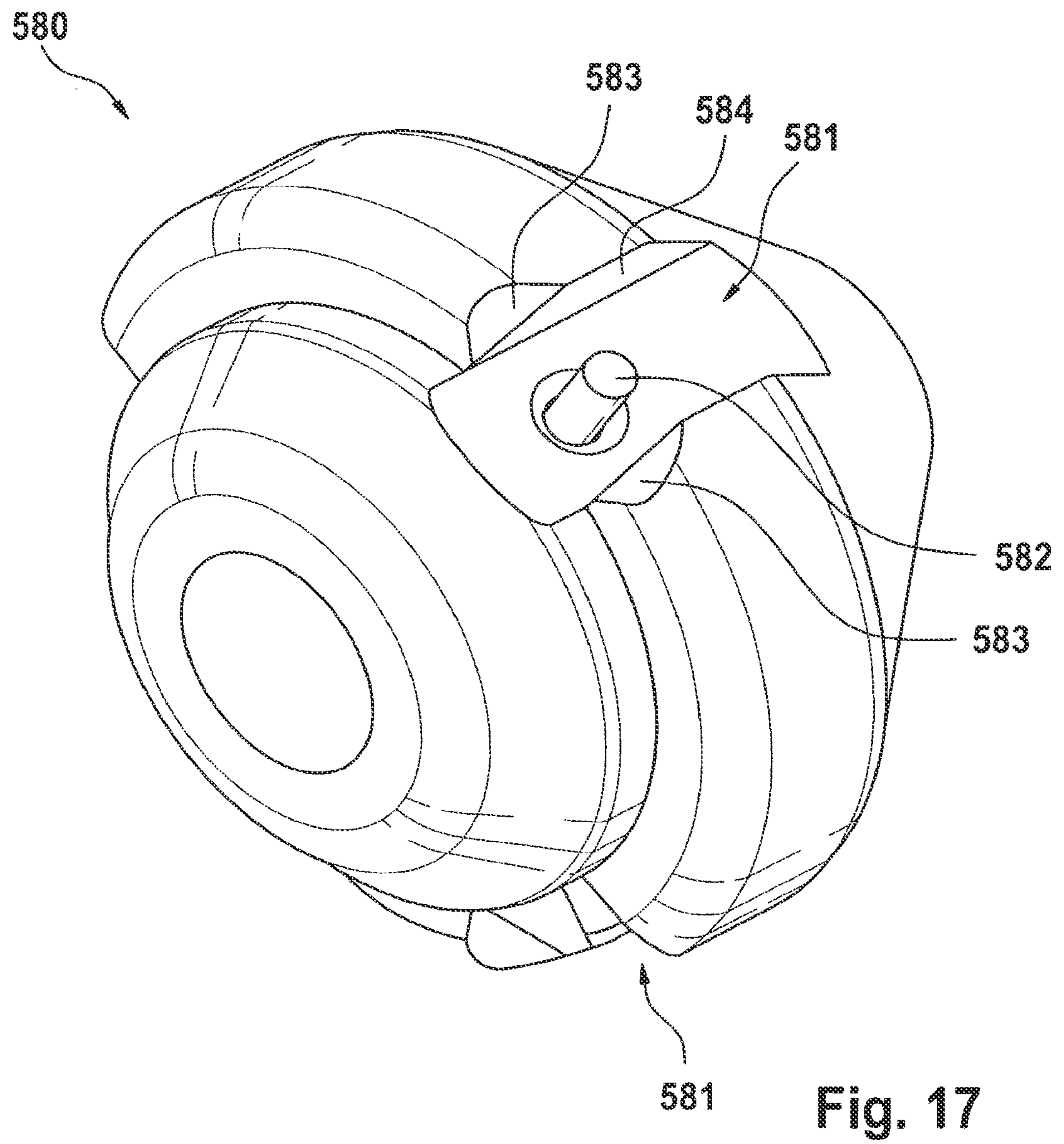

FIG. 17 shows a stent holder 580 to be arranged on a delivery system not shown in the figure. The stent holder 580 comprises axial grooves 581 to receive axial attachment elements of the stent not explicitly shown in this figure, for example elongated cells. Inside each groove 581 there is a pin 582, which projects from the base of the groove 581. Each pin may be generally radially extending, or may project at an inclined angle (inclined with respect to radius and/or axis).

The pins may be inclined towards a radial direction perpendicular to the axial direction by an angle between 0 and 30 degrees, preferably between 0 and 20 degrees or between 0 and 15 degrees, more preferably between 0 and 10 degrees, wherein the value of 0 degree corresponds to a radial extending pin. Preferably the pins are inclined towards away from the aorta side towards the ventrical side. Inclining the pins provides an additional precautionary degree of protections against the stent unintentionally jumping off an engagement with the stent holder during unsheathing or during recapture.

Instead of radially protruding or inclined pins, axially protruding pins may be used instead.

The pins 582 may be embraced by attachment elements which comprise openings.

The grooves 581 comprise ramp surfaces 583 to facilitate the release of the stent component after removing the sheath from the stent. The ramp surfaces 583 are formed by facets on either sides of the groove 581, to facilitate the lifting of the attachment elements and to prevent an eventual blocking of the attachment elements by the walls 584 of the groove 581 when the stent expands. The ramp surfaces 583 may generate a self-lifting effect when contacted by an expanding portion of the stent. Additionally or alternatively, the ramp surfaces 583 may aid separation by small manual manipulation of the stent holder, for example, rotation and/or axial movement.

Medical Uses

According to some embodiments, cardiac stent-valves are provided as cardiac replacement valves. There are four valves in the heart that serve to direct the flow of blood through the two sides of the heart in a forward direction. On the left (systemic) side of the heart are: 1) the mitral valve, located between the left atrium and the left ventricle, and 2) the aortic valve, located between the left ventricle and the aorta. These two valves direct oxygenated blood coming from the lungs through the left side of the heart into the aorta for distribution to the body. On the right (pulmonary) side of the heart are: 1) the tricuspid valve, located between the right atrium and the right ventricle, and 2) the pulmonary valve, located between the right ventricle and the pulmonary artery. These two valves direct de-oxygenated blood coming from the body through the right side of the heart into the pulmonary artery for distribution to the lungs, where it again becomes re-oxygenated to begin the circuit anew.

Problems that can develop with heart valves consist of stenosis, in which a valve does not open properly, and/or insufficiency, also called regurgitation, in which a valve does not close properly. In addition to stenosis and insufficiency of heart valves, heart valves may need to be surgically repaired or replaced due to certain types of bacterial or fungal infections in which the valve may continue to function normally, but nevertheless harbors an overgrowth of bacteria on the leaflets of the valve that may embolize and lodge downstream in a vital artery. In such cases, surgical replacement of either the mitral or aortic valve (left-sided heart valves) may be necessary. Likewise, bacterial or fungal growth on the tricuspid valve may embolize to the lungs resulting in a lung abscess. In such cases replacement of the tricuspid valve even though no tricuspid valve stenosis or insufficiency is present.

According to some embodiments, there is provided a method for replacing a worn or diseased valve comprising transapically implanting a replacement valve, wherein the replacement valve is a stent-valve of the present disclosure. Accordingly, the replacement valve comprises a valve component and a stent component, wherein the valve component is connected to the stent component. Upon implantation, the replacement valve is positioned so that the annular groove receives the annulus of the worn or diseased cardiac valve.

In some cases, the stent-valves of the present disclosure may be designed to be self-positioning under diastolic pressure (i.e., permissible in vivo migration). The placement of the stent-valve may be upstream of the annulus, whereupon when the stent-valve will be locked into position once the annular groove of the stent component receives the annulus. Thus, according to some embodiments, methods are provided for implanting a replacement valve into a heart of a mammal comprising delivering a replacement valve to an implantation site of the heart of the mammal. The implantation site may comprises a release location and a final location; and the release location is spaced apart from the final location (and according to some embodiments, the spacing comprises a predetermined distance) in a blood upflow direction. Releasing the replacement valve at the release location, the replacement valve is able to slide into the final location, generally upon at least one beat of the heart subsequent to the replacement valve being released at the release location.

According to some embodiments, the methods provide that when the replacement valve sliding into the final location, the replacement valve is substantially positioned to the final location.

In some embodiments of the present disclosure, a method is provided for replacing an aortic valve within a human body. A stent-valve may be covered with a sheath in order to maintain the stent-valve in a collapsed configuration. The stent-valve may then be inserted in the collapsed configuration into the human body without contacting the ascending aorta or aortic arch. The stent-valve may be partially expanded by sliding the sheath towards the left ventricle of the heart. This sliding of the sheath towards the left ventricle may cause expansion of a distal end of the stent-valve while the proximal end of the stent-valve remains constrained by the sheath. The sheath may be further slid towards the left ventricle of the heart in order to cause full expansion of the stent-valve. In some embodiments, the stent-valve may be recaptured prior to its full expansion by sliding the sheath in the opposite direction.

In some embodiments, a method for cardiac valve replacement is provided that includes releasing a distal end of a stent-valve from a sheath, where the distal end includes a radiopaque marker positioned thereon. The stent-valve is rotated, if necessary, to orient the stent-valve appropriately with respect to the coronary arteries (e.g., to prevent the commissures from facing the coronary arteries). Stabilization arches 1 of the stent-valve are released from the sheath, in order to cause the stabilization arches 1 to contact the aorta. A upper anchoring crown 3 of the stent-valve is released from the sheath, in order to cause the upper anchoring crown 3 to contact the native valve leaflets. A lower anchoring crown 4 of the stent-valve is released from the sheath, in order to cause the lower anchoring crown 4 to contact an annulus/inflow tract. The lower anchoring crown 4 may be the proximal section of the stent-valve such that releasing the lower anchoring crown 4 causes the stent-valve to be fully released from the sheath. According to some embodiments, a replacement valve for use within a human body is provided, where the replacement valve includes a valve component and a stent component. The stent component also may be used without a connected valve as a stent. The stent devices of the present disclosure may be used to mechanically widen a narrowed or totally obstructed blood vessel; typically as a result of atherosclerosis. Accordingly, the stent devices of the present disclosure may be used in angioplasty procedures. These include: percutaneous coronary intervention (PCI), commonly known as coronary angioplasty, to treat the stenotic (narrowed) coronary arteries of the heart found in coronary heart disease; peripheral angioplasty, performed to mechanically widen the opening in blood vessels other than the coronary arteries.

Thus, it is seen that stent-valves (e.g., single-stent-valves and double-stent-valves) and associated methods and systems for surgery are provided. Although particular embodiments have been disclosed herein in detail, this has been done by way of example for purposes of illustration only, and is not intended to be limiting with respect to the scope of the appended claims, which follow. In particular, it is contemplated by the applicant that various substitutions, alterations, and modifications may be made without departing from the spirit and scope of invention as defined by the claims. Other aspects, advantages, and modifications are considered to be within the scope of the following claims. The claims presented are representative of the inventions disclosed herein. Other, unclaimed inventions are also contemplated. The applicant reserves the right to pursue such inventions in later claims.

In some embodiments a replacement valve for use within a human body is provided comprising a valve component, and a stent component configured to house at least a portion of the valve component comprising a proximal end and a distal end, the stent component further comprising a lower anchoring crown defining an at least partly conical body, wherein the lower anchoring crown defines the proximal end of the stent component, an upper anchoring crown in communication with the lower anchoring crown and defining an at least partly conical body, wherein the conical body of the lower anchoring crown slopes outwardly in the direction of the proximal end, and wherein the conical body of the upper anchoring crown slopes outwardly in the direction of the distal end, the distal stent section defining an at least partly conical body, wherein the distal stent section comprises a conical commissural post section and stabilization arch section, wherein the commissural post section is in communication with the upper anchoring crown, and wherein the stabilization arch section is in communication with commissural post section and defines an at least partly conical, and wherein the stabilization arch section defines the distal end.

Preferably a replacement valve is provided wherein the at least a partially cylindrical body of commissural post section comprises valve fixation elements.

Preferably a replacement valve is provided wherein the conical body of the lower anchoring crown slopes outwardly from an inner diameter D2 to an outer diameter D3 in the direction of the proximal end, wherein the inner diameter D2 is between about 20 mm to about 30 mm, and wherein the outer diameter D3 is between about 22 mm to about 40 mm.

Preferably a replacement valve is provided, wherein the axial distance between the planes of the diameters D2 and D3 in the expanded configuration is between about 3 to about 15 mm.

Preferably a replacement valve is provided, wherein the outward slope of the lower anchoring crown is defined by an angle α2, and wherein α2 is between from about degree to about 50 degree.

Preferably a replacement valve is provided, wherein the conical body of the upper anchoring crown slopes outwardly from an inner diameter D2 to an outer diameter D1 in the direction of the distal end, wherein the inner diameter D2 is between about 20 mm to about 30 mm, and wherein the outer diameter D1 is between about 22 mm to about 40 mm.

Preferably a replacement valve is provided, wherein the axial distance between the planes of the diameters D2 and D1 in the expanded configuration is between about 3 to about 10 mm.

Preferably a replacement valve is provided, wherein the outward slope of the lower anchoring crown is defined by an angle α1, and wherein 1 is between from about 10 degree to about 80 degree.

Preferably a replacement valve is provided, wherein the end of the upper anchoring crown forms a tip, and wherein the tip is bent inwardly toward the longitudinal axis at an angle α3, and wherein α3 is between from about 0 degree to about 180 degree.

Preferably a replacement valve is provided, wherein the length of the combined upper anchoring crown and commissural post section of the stent component H3 is between about 3 to about 50 mm.

Preferably a replacement valve is provided, wherein the length of the stabilization arches and of the stent component H4 is between about 5 to about 50 mm.

Preferably a replacement valve is provided, wherein the lower anchoring crown is configured to create a form fit with an inflow of an aortic valve and thus prevents migration of the stent component and the valve component towards the ascending aorta. Preferably a replacement valve is provided, wherein the upper anchoring crown is configured to create a form fit with an outflow tract and native leaflets of an aortic valve and thus prevent migration of the stent component and the valve component towards the left ventricle.

Preferably a replacement valve is provided, wherein the commissural post section comprises a plurality of commissural posts configured for fixation to commissures of the valve component.

Preferably a replacement valve is provided, wherein the stabilization arches are configured to engage the ascending aorta to orient the stent component, the valve component, and an associated delivery system longitudinally within an aorta/aortic annulus thus preventing tilting of the stent component and the valve component when implanted.

Preferably a replacement valve is provided, wherein the stent component is formed from a single tube or sheet of metal.

Preferably a replacement valve is provided, wherein the lower anchoring crown comprises at least one attachment element for removable attachment to a delivery device.

Preferably a replacement valve is provided, wherein the stent component comprises a plurality of commissural posts for fixation to a corresponding plurality of valve commissures.

Preferably a replacement valve is provided, wherein the conical body of the lower anchoring crown slopes outwardly from an inner diameter D2 to an outer diameter D3 in the direction of the proximal end, wherein the inner diameter D2 is between about 20 mm to about 25 mm, and wherein the outer diameter D3 is between about 26 mm to about 32 mm; wherein the axial distance between the planes of the diameters D2 and D3 in the expanded configuration (H2) is between about 7 to about 11 mm; wherein the outward slope of the lower anchoring crown is defined by an angle α2, and wherein α 2 is between from about 15 degree to about 25 degree; wherein the conical body of the upper anchoring crown slopes outwardly from an inner diameter D2 to an outer diameter D1 in the direction of the distal end, wherein the inner diameter D2 is between about 20 mm to about 25 mm, and wherein the outer diameter D1 is between about 26 mm to about 31 mm; wherein the axial distance between the planes of the diameters D2 and D1 in the expanded configuration (H1) is between about 4 to about 8 mm; wherein the outward slope of the lower anchoring crown is defined by an angle α1, and wherein 1 is between from about 45 degree to about 65 degree; wherein the end of the upper anchoring crown forms a tip, and wherein the tip is bent inwardly toward the longitudinal axis at an angle α3, and wherein α3 is between from about 45 degree to about 65 degree; wherein the length of the combined upper anchoring crown and commissural posts of the stent component (H3) is between about 11 to about 15 mm; wherein the length of the stabilization arches of the stent component (H4) is between about 14 to about 22 mm; and wherein the stabilization arches of the stent component expands outwardly at an angle α4 from a longitudinal axis toward the second distal end of the replacement valve, wherein α4 is between about 5 degree to about 15 degree.

Preferably a replacement valve is provided, wherein the conical body of the lower anchoring crown slopes outwardly from an inner diameter D2 to an outer diameter D3 in the direction of the proximal end, wherein the inner diameter D2 is between about 21 mm to about 26 mm, and wherein the outer diameter D3 is between about 27 mm to about 33 mm; wherein the axial distance between the planes of the diameters D2 and D3 in the expanded configuration (H2) is between about 8 to about 12 mm; wherein the outward slope of the lower anchoring crown is defined by an angle α2, and wherein α2 is between from about 15 degree to about 25 degree; wherein the conical body of the upper anchoring crown slopes outwardly from an inner diameter D2 to an outer diameter D1 in the direction of the distal end, wherein the inner diameter D2 is between about 21 mm to about 26 mm, and wherein the outer diameter D1 is between about 27 mm to about 32 mm; wherein the axial distance between the planes of the diameters D2 and D1 in the expanded configuration (H1) is between about 4 to about 8 mm; wherein the outward slope of the lower anchoring crown is defined by an angle α1, and wherein 1 is between from about 45 degree to about 65 degree; wherein the end of the upper anchoring crown forms a tip, and wherein the tip is bent inwardly toward the longitudinal axis at an angle α3, and wherein α3 is between from about 45 degree to about 65 degree; wherein the length of the combined upper anchoring crown and commissural posts section of the stent component (H3) is between about 13 to about 17 mm; wherein the length of the stabilization arches and of the stent component (H4) is between about 15 to about 23 mm; and wherein the stabilization arches of the stent component expands outwardly at an angle α4 from a longitudinal axis toward the second distal end of the replacement valve, wherein α4 is between about 5 degree to about 15 degree.

Preferably a replacement valve is provided, wherein the conical body of the lower anchoring crown slopes outwardly from an inner diameter D2 to an outer diameter D3 in the direction of the proximal end, wherein the inner diameter D2 is between about 22 mm to about 27 mm, and wherein the outer diameter D3 is between about 28 mm to about 34 mm; wherein the axial distance between the planes of the diameters D2 and D3 in the expanded configuration (H2) is between about 9 to about 13 mm; wherein the outward slope of the lower anchoring crown is defined by an angle α2, and wherein α2 is between from about 15 degree to about 25 degree; wherein the conical body of the upper anchoring crown slopes outwardly from an inner diameter D2 to an outer diameter D1 in the direction of the distal end, wherein the inner diameter D2 is between about 22 mm to about 27 mm, and wherein the outer diameter D1 is between about 28 mm to about 33 mm; wherein the axial distance between the planes of the diameters D2 and D1 in the expanded configuration (H1) is between about 4 to about 8 mm; wherein the outward slope of the lower anchoring crown is defined by an angle α1, and wherein 1 is between from about 45 degree to about 65 degree; wherein the end of the upper anchoring crown forms a tip, and wherein the tip is bent inwardly toward the longitudinal axis at an angle α3, and wherein α3 is between from about 45 degree to about 65 degree; wherein the length of the combined upper anchoring crown and commissural post section of the stent component (H3) is between about 15 to about 19 mm; wherein the length of the stabilization arches and of the stent component (H4) is between about 16 to about 24 mm; and wherein the stabilization arches of the stent component expands outwardly at an angle α4 from a longitudinal axis toward the second distal end of the replacement valve, wherein α4 is between about 5 degree to about 15 degree.

In some embodiments a system for replacing a valve within a human body is provided comprising a delivery device and a replacement valve for use within a human body comprising a valve component, and a stent component configured to house at least a portion of the valve component comprising a proximal end and a distal end, the stent component further comprising a lower anchoring crown defining an at least partly conical body, wherein the lower anchoring crown defines the proximal end of the stent component, an upper anchoring crown in communication with the lower anchoring crown and defining an at least partly conical body, wherein the conical body of the lower anchoring crown slopes outwardly in the direction of the proximal end, and wherein the conical body of the upper anchoring crown slopes outwardly in the direction of the distal end, a distal stent section defining an at least partly conical body, wherein the distal stent section comprises a conical commissural post section and stabilization arch section, wherein the commissural post section is in communication with the upper anchoring crown; and wherein the stabilization arch section is in communication with commissural post section and defines an at least partly conical, and wherein the stabilization arch section defines the distal end, the stent component having a central, longitudinal axis and comprising at least one attachment element for removable attachment to a delivery device, wherein the at least one attachment element is located at a proximal end of the stent component, wherein the proximal end is defined as the end toward the left ventricle when delivered from a transapical approach.

Preferably a system is provided, wherein the at least one attachment element is formed generally in the shape of a hook.

Preferably a system for replacing a valve within a human body comprising a delivery device and a replacement valve is provided, wherein the delivery device comprises: an inner member comprising a guide wire lumen and a stent holder; and an outer member comprising a sheath; wherein the stent holder comprises a groove for receiving the attachment element of the stent component, and wherein the inner member and the outer member are co-axially positioned and slidable relative to one another in order to transition from a closed position to an open position, such that in the closed position the sheath encompasses at least a portion of the stent-valve still attached to the stent holder constraining expansion of the stent-valve, and such that in the open position the outer sheath does not constrain expansion of the stent-valve and the stent-valve detaches from the stent holder and expands to an expanded configuration.

Preferably a system for replacing a valve within a human body comprising a delivery device and a replacement valve is provided, wherein release of the stent-valve from the stent holder is facilitated by slight rotation of the stent holder relative to the attachment element.

In some embodiments a method for replacing an aortic valve within a human body is provided, the method comprising: covering the replacement valve as described above with a sheath in order to maintain the replacement valve in a collapsed configuration, transapically inserting the replacement valve still in the collapsed configuration into the human body, partially expanding the replacement valve by sliding the sheath towards the left ventricle of the heart, wherein said sliding of the sheath towards the left ventricle causes expansion of a distal end of the replacement valve while the proximal end of the replacement valve remains constrained by the sheath, and further sliding the sheath towards the left ventricle of the heart in order to substantially release the entire replacement valve such that the replacement valve is allowed to expand to an expanded configuration.

In some embodiments a method is provided further comprising sliding the sheath in the opposite direction prior to said full expansion in order to recapture the replacement valve within the sheath.

In some embodiments a method is provided, the method comprising releasing a distal end of the replacement valve as described above from a sheath, wherein the distal end comprises a radiopaque marker, rotating the replacement valve, if necessary, to orient the replacement valve appropriately with respect to the coronary arteries, releasing arches of the replacement valve from the sheath, in order to cause the arches to contact the aorta, releasing a first conical crown of the replacement valve from the sheath, in order to cause the first conical crown to contact native valve leaflets, and releasing a second crown of the replacement valve from the sheath, in order to cause the second crown to contact an annulus/inflow tract, wherein the second crown comprises the proximal section of the replacement valve and said releasing of the second crown comprises fully releasing the replacement valve from the sheath.

In some embodiments a method for cardiac valve replacement is provided, the method comprising releasing a distal end of the replacement valve as described above from a sheath, wherein the distal end comprises a radiopaque marker and a plurality of arches, rotating the replacement valve, if necessary, to orient the replacement valve appropriately with respect to the coronary arteries, releasing the arches of the replacement valve from the sheath, in order to cause the arches to contact an area above a native valve, releasing a first conical crown portion of the replacement valve from the sheath, in order to cause the first conical crown to contact the native valve leaflets, and releasing a second crown portion of the replacement valve from the sheath, in order to cause the second crown to contact an annulus/inflow tract of the native valve, wherein the second crown is the proximal section of the replacement valve and said releasing the second crown comprises fully releasing the replacement valve from the sheath.

In some embodiments a method for cardiac valve replacement is provided, the method comprising transapically implanting the replacement valve as described above, wherein the replacement valve comprises a valve component and a stent component to which the valve component is affixed thereto, the stent component comprising a longitudinal axis, a lower anchoring crown including a substantially conical shape having a narrow end, a broad end and a predetermined first height, and an upper anchoring crown including a substantially conical shape having a narrow end, a broad end and a predetermined second height, wherein a center of each of the lower anchoring crown and the upper anchoring crown are arranged to align substantially with the longitudinal axis, the narrow ends of the lower anchoring crown and upper anchoring crown are arranged to meet forming an annular groove to receive the annulus of worn or diseased cardiac valve at an implantation site of the heart, the first height of the lower anchoring crown is greater than the second height of the upper anchoring crown, and positioning the replacement valve so that the annular groove receives the annulus of the worn or diseased cardiac valve.

What is claimed:

1. A replacement valve configured to be used within a human body comprising:

a valve component; and a stent component having an inflow end and an outflow end and a central longitudinal axis extending therebetween, the stent component being configured to house at least a portion of the valve component, the stent component further comprising:

a lower anchoring crown section having a first diameter, wherein the lower anchoring crown section defines the inflow end of the stent component;

a middle section having a second diameter smaller than the first diameter; and an outflow stent section comprising an at least partly conical body having a stabilizing arch section and a commissural post section including a plurality of commissure posts, the outflow stent section defining the outflow end of the stent component, wherein a free end of the outflow stent section includes the stabilizing arch section having a plurality of closed loop arches extending toward and defining the outflow end, the stabilizing arch section bulging first radially outward to define a third diameter and then curving radially inward toward the central longitudinal axis at the outflow end to define a fourth diameter smaller than the third diameter, wherein the third and fourth diameters are adjacent the outflow end;

wherein the stent component defines a plurality of closed cells including at least one large cell positioned between adjacent commissure posts that is larger than a remainder of the plurality of closed cells.

2. The replacement valve of claim 1, further comprising an outer seal disposed on an outer surface of the lower anchoring crown section.

3. The replacement valve of claim 2, further comprising an inner seal disposed on an inner surface of the lower anchoring crown section.

4. The replacement valve of claim 1, wherein the lower anchoring crown section and the outflow stent section each slope radially outward from a middle section of the stent component.

5. The replacement valve of claim 1, wherein the plurality of closed cells includes a plurality of diamond shaped closed cells in the lower anchoring crown section.

6. The replacement valve of claim 5, wherein the inflow end of the stent component is defined by lower points of the plurality of diamond shaped closed cells.

7. The replacement valve of claim 1, further comprising an upper anchoring crown section disposed between the lower anchoring crown section and the outflow stent section, the upper anchoring crown section having a fifth diameter larger than the first and second diameters.

8. The replacement valve of claim 7, wherein the at least partly conical body of the outflow stent section slopes outwardly to the third diameter in the direction towards the outflow end.

9. A replacement valve configured to be used within a human body comprising:

a valve component; and a stent component having an inflow end and an outflow end and a central, longitudinal axis extending therebetween, and being configured to house at least a portion of the valve component, the stent component further comprising:

a lower anchoring crown section having a first diameter at the inflow end of the stent component;

a middle section having a second diameter smaller than the first diameter, the lower anchoring crown section sloping outwardly from the first second diameter to a third the first diameter at the inflow end; and an outflow stent section comprising an at least partly conical body having a stabilizing arch section and a commissural post section including a plurality of commissure posts, the outflow stent section defining the outflow end of the stent component, wherein a free end of the outflow stent section includes the stabilizing arch section having a plurality of closed loop arches extending toward and defining the outflow end, wherein the stabilizing arch section bulges radially outwardly relative to the longitudinal axis from the commissural post section towards the outflow end and thereafter slopes radially inwards at the outflow end;

wherein the stent component defines a plurality of closed cells including at least one large cell positioned between adjacent commissure posts that is larger than a remainder of the plurality of closed cells.

10. The replacement valve of claim 9, further comprising an outer seal disposed on an outer surface of the lower anchoring crown section.

11. The replacement valve of claim 10, further comprising an inner seal disposed on an inner surface of the lower anchoring crown section.

12. The replacement valve of claim 9, wherein the lower anchoring crown section and the outflow stent section each slope radially outward from a middle section of the stent component.

13. The replacement valve of claim 9, wherein the plurality of closed cells includes a plurality of diamond shaped closed cells in the lower anchoring crown section.

14. The replacement valve of claim 13, wherein the inflow end of the stent component is defined by lower points of the plurality of diamond shaped closed cells.

15. The replacement valve of claim 9, further comprising an upper anchoring crown section disposed between the lower anchoring crown section and the outflow stent section, the upper anchoring crown section having a third diameter larger than the second diameter.

16. The replacement valve of claim 15, wherein the at least partly conical body of the upper anchoring crown slopes outwardly in a direction towards the outflow end.

17. A replacement valve configured to be used within a human body comprising:

a valve component; and a stent component having an inflow end and an outflow end and a central longitudinal axis extending therebetween, the stent component defining a plurality of closed cells and being configured to house at least a portion of the valve component, the stent component further comprising:

a lower anchoring crown section having a first diameter and defining the inflow end of the stent component, wherein the plurality of closed cells includes a plurality of diamond shaped closed cells in the lower anchoring crown section, wherein the inflow end is defined by lower points of the plurality of diamond shaped closed cells; and an outflow stent section comprising an at least partly conical body having a stabilizing arch section including a plurality of closed loop arches defining the outflow end of the stent component, and a commissural post section including a plurality of commissure posts, the plurality of closed loop arches curving first radially outward to define a second diameter and then curving radially inward toward the central longitudinal axis at the outflow end of the stent component to define a third diameter smaller than the second diameter, wherein the second and third diameters are adjacent the outflow end;

wherein the plurality of closed cells includes at least one large cell positioned between adjacent commissure posts that is larger than a remainder of the plurality of closed cells.

18. The replacement valve of claim 17, wherein the stabilizing arch section extends from the commissural post section in a direction towards the outflow end.

19. The replacement valve of claim 17, further comprising a seal disposed on an outer surface of the lower anchoring crown section.

* * * * *